US011931353B2

(12) United States Patent
Yue et al.

(10) Patent No.: US 11,931,353 B2
(45) Date of Patent: Mar. 19, 2024

(54) METHODS OF PREVENTING OR TREATING FLAVIVIRUS VIRUS INFECTIONS AND METHODS OF INHIBITING THE ENTRY OF FLVIVIRUS, ENTEROVIRUS OR LENTIVIRUS INTO HOST CELLS

(71) Applicant: City University of Hong Kong, Kowloon (HK)

(72) Inventors: Jianbo Yue, Kowloon Tong (HK); Lihong Huang, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 11 days.

(21) Appl. No.: 17/738,291

(22) Filed: May 6, 2022

(65) Prior Publication Data

US 2022/0257588 A1 Aug. 18, 2022

Related U.S. Application Data

(63) Continuation of application No. 16/559,869, filed on Sep. 4, 2019, now Pat. No. 11,357,771.

(51) Int. Cl.

| | |
|---|---|
| ***A61K 31/4725*** | (2006.01) |
| ***A61K 31/352*** | (2006.01) |
| ***A61K 31/47*** | (2006.01) |
| ***A61K 31/472*** | (2006.01) |
| ***A61K 31/4741*** | (2006.01) |
| ***A61K 31/55*** | (2006.01) |
| ***A61P 31/14*** | (2006.01) |

(52) U.S. Cl.

CPC ........ *A61K 31/4725* (2013.01); *A61K 31/352* (2013.01); *A61K 31/47* (2013.01); *A61K 31/472* (2013.01); *A61K 31/4741* (2013.01); *A61K 31/55* (2013.01); *A61P 31/14* (2018.01)

(58) Field of Classification Search

CPC .................................................. A61K 31/4725

See application file for complete search history.

(56) References Cited

U.S. PATENT DOCUMENTS

| | | | | |
|---|---|---|---|---|
| 11,357,771 B2 * | 6/2022 | Yue | A61K 31/55 | |
| 2014/0378435 A1 * | 12/2014 | Davey | A61K 31/366 | 435/375 |

OTHER PUBLICATIONS

Liou et al., Differential effects of triptolide and tetrandrine on activation of COX-2, Nf-Kb, and AP-1 and virus production in dengue virus-infected human lung cells, European Journal of Pharmacology, vol. 589, Issues 1-3, Jul. 28, 2008, pp. 288-298.*

* cited by examiner

*Primary Examiner* — Svetlana M Ivanova

(74) *Attorney, Agent, or Firm* — Renner, Kenner, Greive, Bobak, Taylor & Weber

(57) ABSTRACT

A method of preventing or treating a subject suffering from a flavivirus infection by administering an effective amount of berbamine or its analogue to the subject, berbamine has a structure of Formula (I), wherein the flavivirus infection is caused by Japanese encephalitis virus, Zika virus or Dengue virus. A method of inhibiting the entry of a flavivirus, an enterovirus and/or a lentivirus into host cells includes contacting the host cells with an effective amount of berbamine of its analogue, berbamine has a structure of Formula (I), wherein the flavivirus is Japanese encephalitis virus, Zika virus or Dengue virus.

8 Claims, 16 Drawing Sheets
(13 of 16 Drawing Sheet(s) Filed in Color)

METHODS OF PREVENTING OR TREATING FLAVIVIRUS VIRUS INFECTIONS AND METHODS OF INHIBITING THE ENTRY OF FLVIVIRUS, ENTEROVIRUS OR LENTIVIRUS INTO HOST CELLS

TECHNICAL FIELD

The present invention relates to a method of preventing or treating a subject suffering from an infection caused by a RNA virus including infections caused by a positive single-stranded RNA virus. The method is useful in prevent or treatment of an infection caused by a flavivirus, an enterovirus or a lentivirus.

BACKGROUND OF THE INVENTION

RNA viruses, particularly positive single-stranded RNA viruses, such as viruses from Flaviviridae, Enterovirus and Coronavirus are expanding threat in public health. West Nile virus, Japanese encephalitis virus (JEV), Zika virus (ZIKV), Dengue virus (DENV), and enterovirus A17 (EV-A17) are considered as the leading causes of human and animal infectious diseases in the world. The morbidity and mortality of related illness caused by these viruses have been increasing every year. West Nile virus has recently spread from the Mediterranean Basin to the Western Hemisphere and now accounts for thousands of sporadic encephalitis cases each year. Also, Japanese encephalitis have caused thousands of deaths each year in a wide range of endemic areas.

Although there are some commercially available vaccines against yellow fever, Japanese encephalitis and neonatal encephalitis, there are few or almost no effective clinical treatment against flaviviruses or enteroviruses. For example, patients suffering from serious flavivirus or enterovirus infection may only receive supportive care including administration with intravenous fluids, hospitalization, respiratory support, and prevention of secondary infections. There is currently a lack of effective remedy in treating RNA virus infection particularly caused by flaviviruses and enteroviruses.

Accordingly, there remains a strong need for novel compounds which are useful in the prevention or treatment of RNA viral infection particularly flavivirus infection.

SUMMARY OF THE INVENTION

In a first aspect, the present invention pertains to a method of preventing or treating a subject suffering from a flavivirus infection by administering an effective amount of berbamine or its analogue to the subject, berbamine has a structure of Formula (I):

Formula (I)

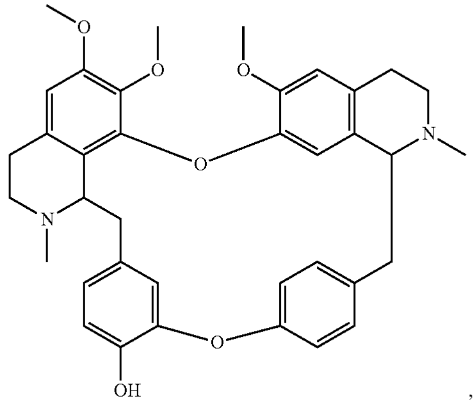

, wherein the flavivirus infection is caused by Japanese encephalitis virus, Zika virus or Dengue virus.

In a second aspect, the present invention pertains to a method of inhibiting the entry of a flavivirus into host cells, comprising contacting the host cells with an effective amount of berbamine or its analogue, berbamine has a structure of Formula (I):

Formula (I)

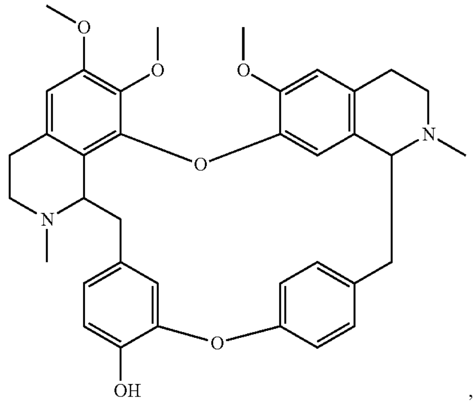

, wherein the flavivirus is Japanese encephalitis virus, Zika virus or Dengue virus.

In a third aspect, the present invention relates to a method of inhibiting the entry of an enterovirus and/or a lentivirus into host cells, comprising contacting the host cells with an effective amount of berbamine or its analogue as described above.

In a fourth aspect, the present invention relates to use of berbamine or its analogue in prevention or treatment of a RNA virus infection, particularly but not exclusively a flavivirus infection, an enterovirus infection or a lentivirus infection.

Still further, berbamine or its analogue may be used in the preparation of a medicament for preventing or treating a RNA virus infection, particularly but not exclusively a flavivirus infection, an enterovirus infection or a lentivirus infection.

The inventors unexpectedly found that benzylisoquinoline alkaloids of the present invention, i.e. berbamine and its analogues, have an antiviral effect, particularly against RNA virus infections such as a flavivirus infection, an enterovirus infection or a lentivirus infection. The inventors found that berbamine and its analogues are capable of inhibiting the entry of the viruses into host cells thereby protecting the cells from being infected. Mice infected with the virus particularly flavivirus were also found to have higher survival rate after treatment with the benzylisoquinoline alkaloids. Accordingly, the present invention provides effective compounds for treating and/or preventing flavivirus infection, particularly Japanese encephalitis virus infection, Zika virus infection and/or Dengue virus infection.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
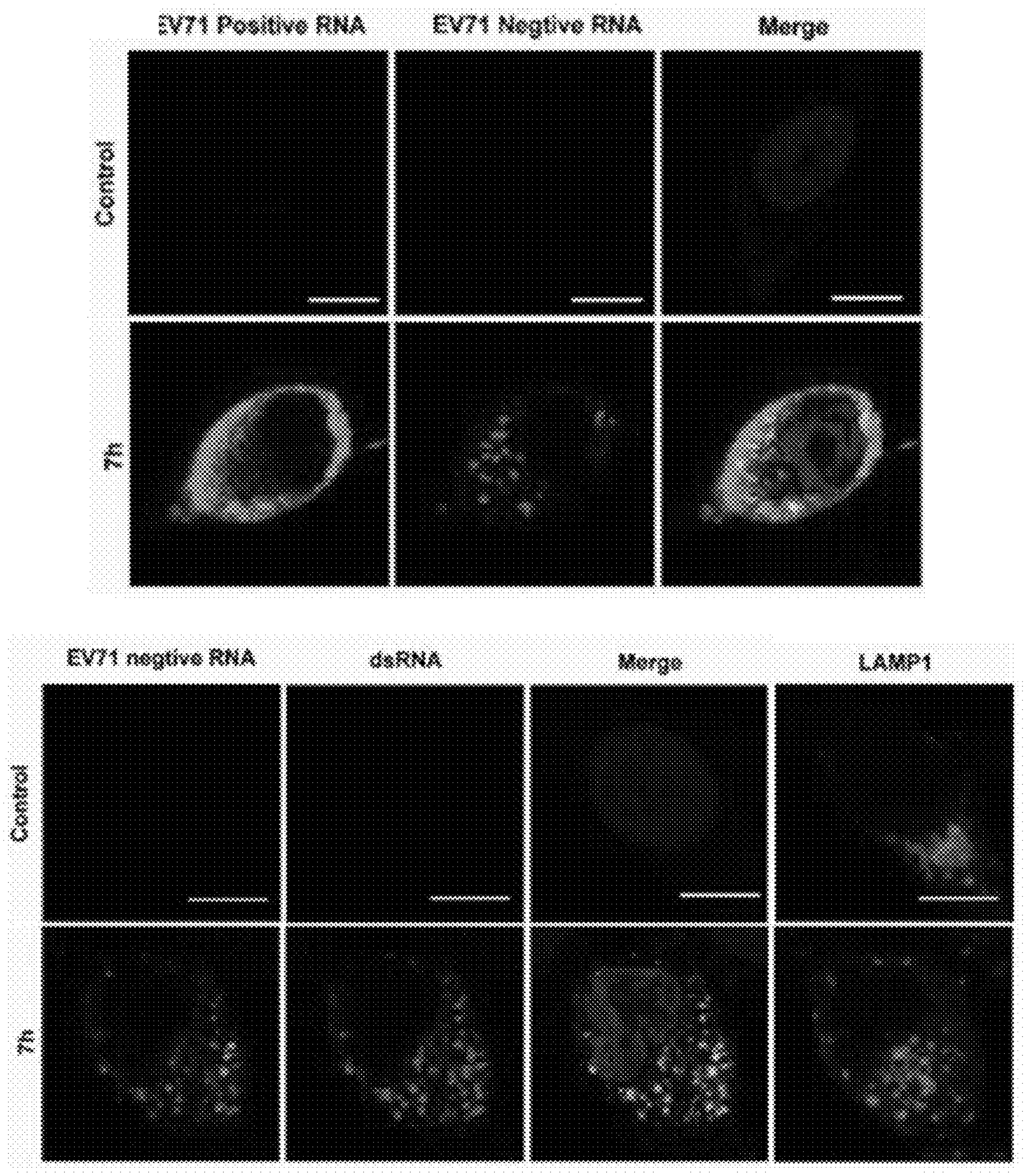
FIG. 1A shows the microscopic images of HeLa cells obtained after in situ hybridization of EV-71 positive strand RNA and EV71 negative strand RNA and immunostaining of dsRNA or LAMP1, in which the HeLa cells were infected with EV-71 (MOI=1) for 7 h and EV-71 virions were observed.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a", "an", and "the" are intended to include the singular and plural forms unless the context clearly indicates otherwise.

The present invention in the first aspect provides a method of preventing or treating a subject suffering from a RNA virus infection particularly an infection caused by a positive single-stranded RNA virus. The RNA virus may be a flavivirus, an enterovirus or a lentivirus. In embodiments herein, the method is suitable for preventing or treating a subject suffering from a flavivirus infection by administering an effective amount of berbamine or its analogue to the subject.

In an embodiment, the flavivirus is Japanese encephalitis virus, Zika virus or Dengue virus. In an alternative embodiment, the flavivirus may be selected from the group consisting of West Nile virus, Murray Valley encephalitis virus, and Yellow Fever virus.

Berbamine and its analogue can be classified as bisbenzylisoquinoline alkaloids including two benzylisoquinoline moieties linked through diphenyl ether, benzyl phenyl ether or biphenyl bonds. Berbamine and its analogue may be artificially synthesized or may be a naturally occurring compound derived from a plant material, a fungus or the like.

Berbamine has a structure of Formula (I)

Formula (I)

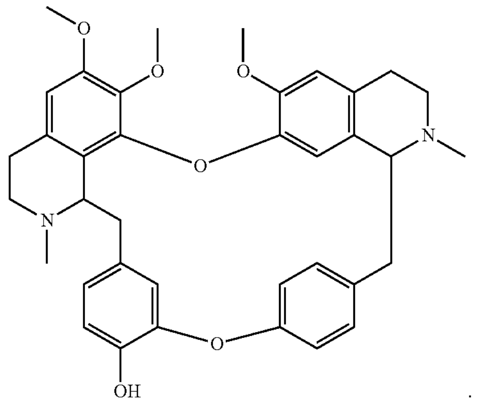

Analogues of berbamine generally share a core structure of Formula (Ib):

Formula (Ib)

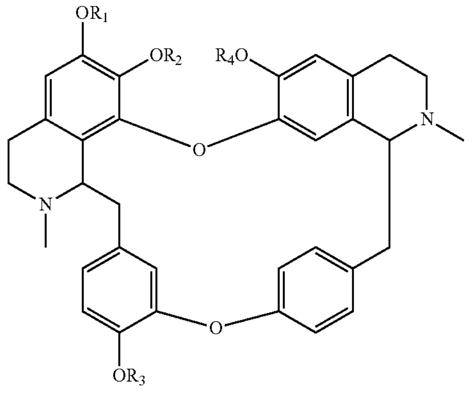

wherein $R_1$, $R_2$, $R_3$, $R_4$ are independently selected from a hydrogen atom, a C1-C3 alkyl group, a halogen atom or a nitrogen containing group, and with the provision that the analogue is not tetrandrine. C1-C3 alkyl group may be any of a methyl group, an ethyl group, a propyl group, an isopropyl group, or a cyclopropyl group. The halogen atom may be selected from the group consisting of fluorine, chlorine, and bromine.

In an embodiment, the analogue of berbamine preferably has a structure of Formula (II), (Iii), or (IV):
Formula (II)
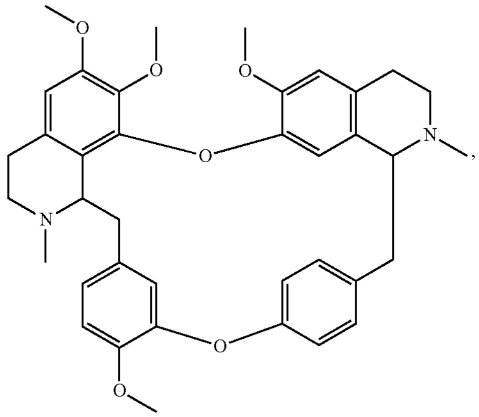
Formula (III)
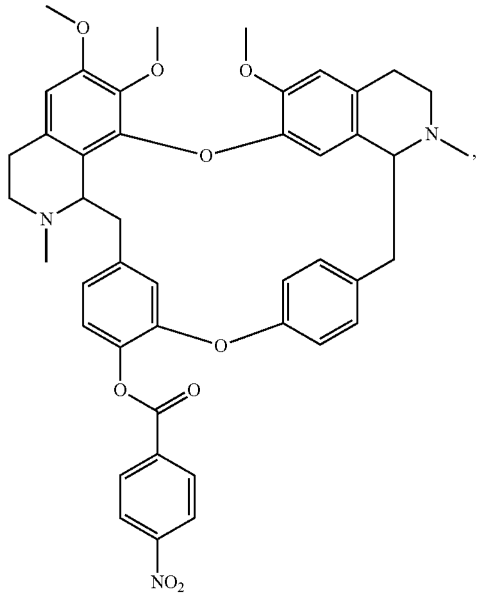
or
Formula (IV)
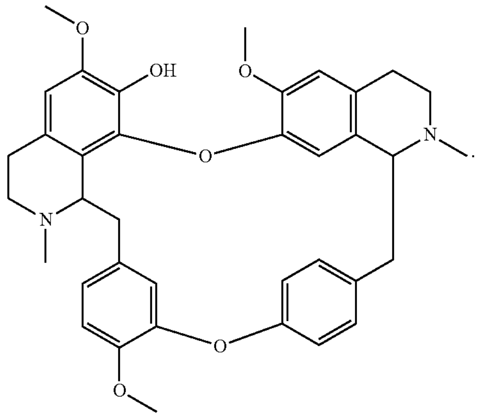
In an embodiment, the analogue of berbamine has a structure of Formula (IIb), (IIIb), or (IVb):
Formula (IIb)
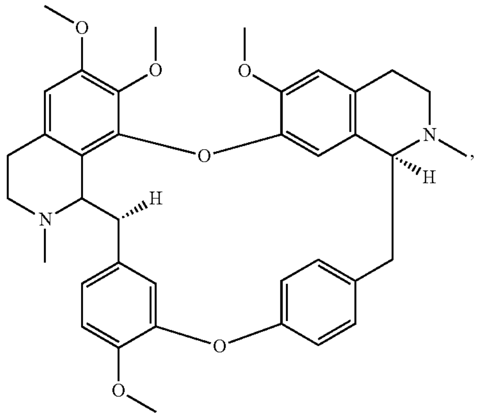
Formula (IIIb)
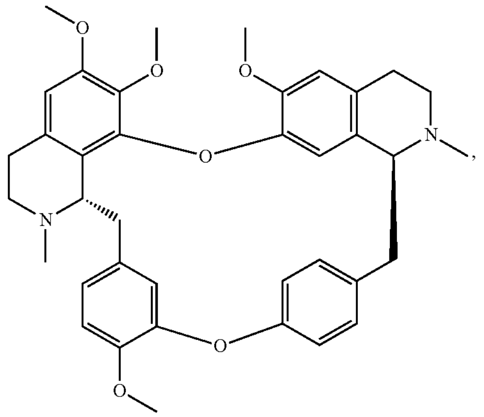
or
Formula (IVb)
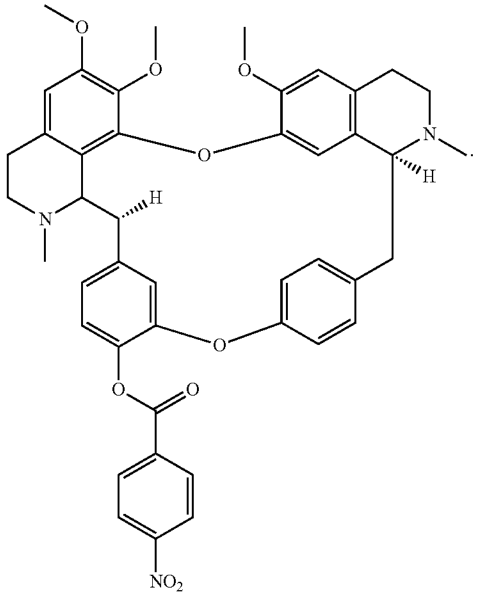

The inventors found that berbamine and its analogues as disclosed above are effective against flavivirus for example by inhibiting the entry of the virus into the host cells, and/or protecting a subject from being infected at a particular dose. They are potential anti-viral agents particularly anti-flavivirus agents.

Berbamine is found to be exceptionally suitable for use in prevention and treatment of flavivirus infection. The inventors proved that berbamine has an inhibitory effect against at least JEV, ZIKV, DENV-2, EV-71 and lentivirus.

Berbamine and its analogues as disclosed herein may inhibit the entry of an enterovirus and/or a lentivirus into host cells of the subject, thereby boosting the immunity of the subject against various types of virus. The inventors also found that their antiviral effects are not cell-specific.

It would be appreciated that salts or solvates of berbamine and its analogues are also included in the scope, and may be used for preventing or treating the same virus infection.

The method of the present invention may be used as a precautionary method to prevent a subject from suffering a flavivirus infection as the method is useful in boosting the immune system, inhibiting the entry of the virus into host cells, and/or inhibiting the interaction between the virus and the host cells. It would be appreciated that the treatment of flavivirus infection may involve inhibition of the viral proteins in the infected subject, killing of the virus, alleviating symptoms caused by the virus, and/or inhibiting the synthesis of the virus, or the combinations thereof.

The term "subject" in particular refers to an animal or human, in particular a mammal and most preferably human. In an embodiment, the subject is susceptible to a flavivirus infection, or is suffering from a flavivirus infection. In a further embodiment, the subject is suffering from two different types of RNA virus infections. In an example embodiment, the subject is susceptible to or suffering from an enterovirus infection, lentivirus infection or a combination thereof.

The expression "effective amount" generally denotes an amount sufficient to produce therapeutically desirable results, wherein the exact nature of the result varies depending on the specific condition which is treated. Berbamine or its analogue may be contained in a composition, in particular a pharmaceutical composition, in an effective amount, i.e. an amount suitable to treat or prevent the RNA virus infection particularly flavivirus infection, enterovirus infection or lentivirus infection in a subject, in particular a mammal, which also depends on the frequency and number of compositions to be administered. In an embodiment, the subject is a mammal and berbamine or its analogue may be administered to the subject at a dose of about 20 mg/kg to about 50 mg/kg, or above. In other embodiment, the subject is human and berbamine or its analogue may be administered to the subject at a dose of about 20 mg/kg to about 50 mg/kg, or above.

When berbamine or its analogue is provided in a pharmaceutical composition to a subject, the skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

In embodiments of the present invention, berbamine or its analogue as disclosed herein is administered to the subject by a route selected from a group consisting of oral delivery, intravenous delivery, intradermal delivery, intraperitoneal delivery and intramuscular delivery. The person skilled in the art is able to formulate berbamine or its analogue in a pharmaceutical composition according to the specific flavivirus infection and the disclosure herein.

In addition, berbamine or its analogue may be administered in combination with a compound selected from the group consisting of the following compounds and a derivative thereof:

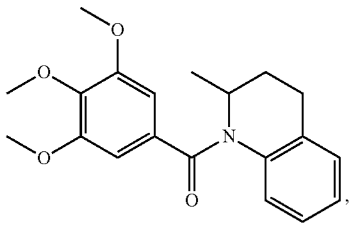

,

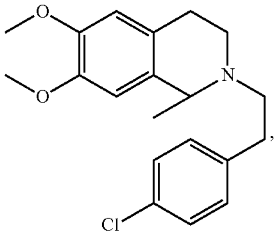

,

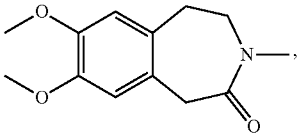

,

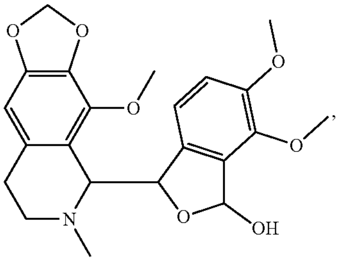

,

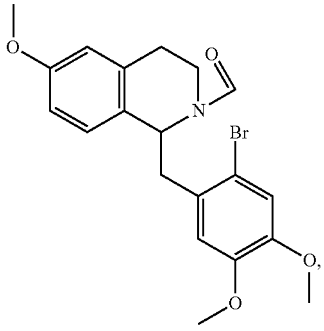

,

-continued

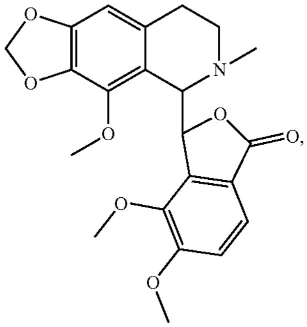

,

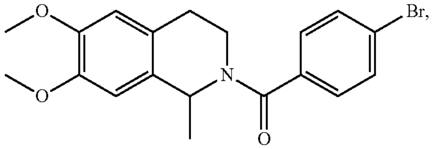

,

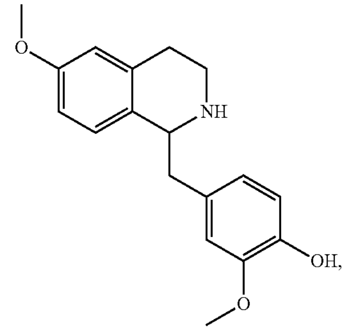

,

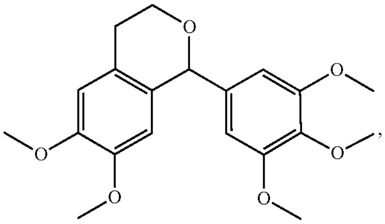

,

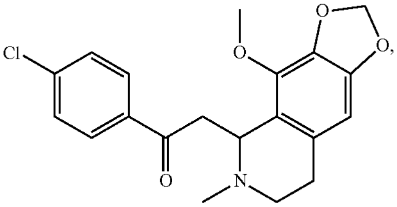

,

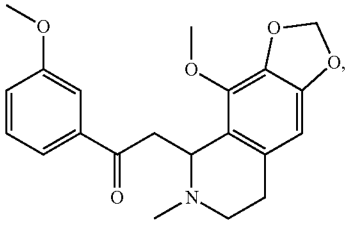

,

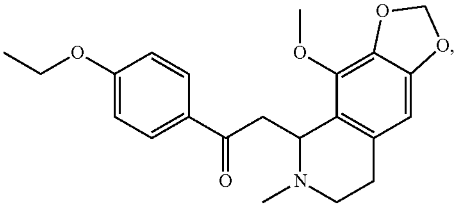

, and

-continued

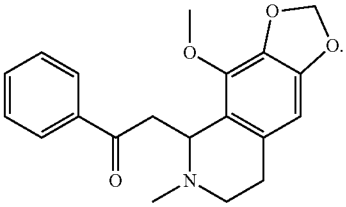

.

The above compounds were identified and considered to have a similar 3D conformation with berbamine. Particularly, these compounds were identified using berbamine as reference and therefore it is believed that they can achieve similar or identical inhibitory effect as berbamine. It has also been determined that the above compounds have anti-viral effect, which is described in the examples and the effect is also represented in the corresponding figure. The above compounds can be provided in any salt form suitable for administration or use.

It would be appreciated that the above compounds may be used alone for treating or preventing RNA virus infection such as flavivirus infection as they demonstrated antiviral effect particularly by inhibiting the entry of flavivirus into host cells. Therefore, the present invention also pertains to a method of preventing or treating a subject suffering from a flavivirus infection by administering the subject with an effective amount of a compound selected from the group consisting of the following compounds and a derivative thereof:

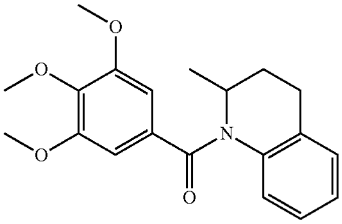 [SMILES: COc1cc(C(=O)N2c3ccccc3CCC2C)cc(OC)c1OC]

,

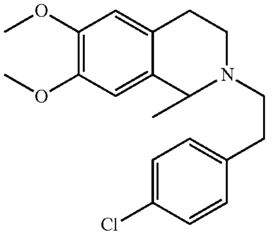 [SMILES: COc1cc2c(cc1OC)C(C)N(CCc1ccc(Cl)cc1)CC2]

,

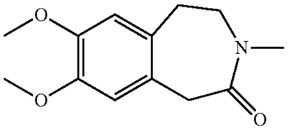

,

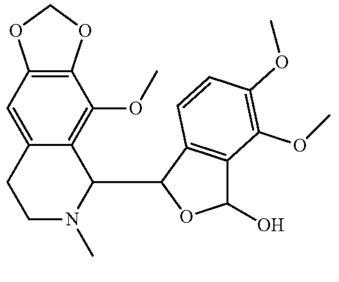

,

-continued

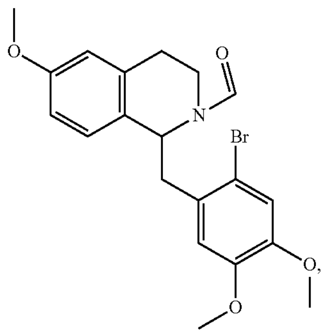

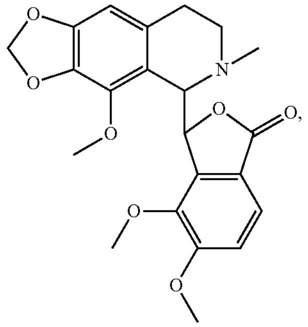

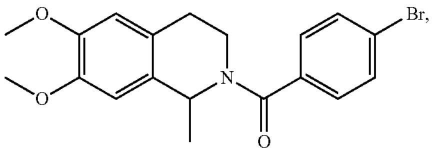

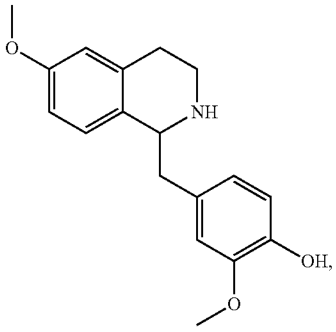

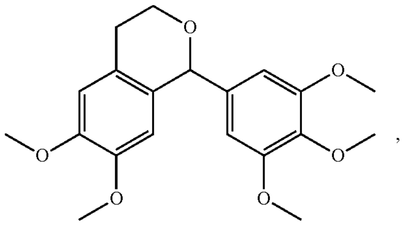

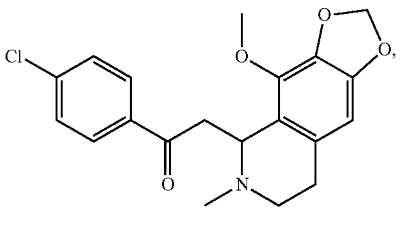

-continued

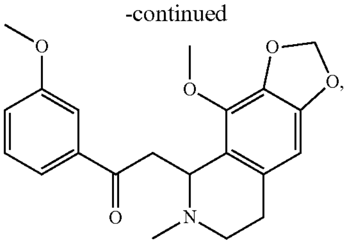

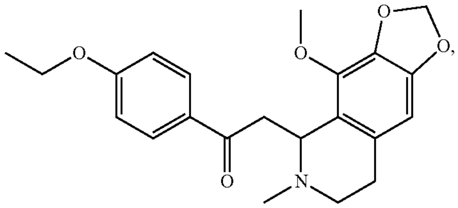

and

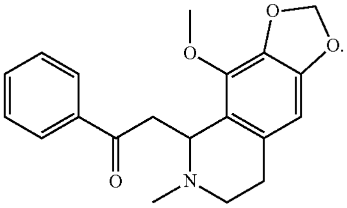

These compounds may be used to prepare a medicament for preventing or treating the infection as described above.

The present invention further pertains to a method of inhibiting the entry of a flavivirus, particularly Japanese encephalitis virus, Zika virus or Dengue virus, into host cells, comprising contacting the host cells with an effective amount of berbamine or its analogue. The flavivirus is as described above. Particularly, the flavivirus is Japanese encephalitis virus or Zika virus. Berbamine and its analogue are also as described above.

The method may comprise a step of incubating the host cells with a medium containing berbamine or its analogue for a period of time such as for at least 0.5 h, at least 1 h, at least 1.5 h, or above.

In an embodiment, berbamine or its analogue may further inhibit the entry of an enterovirus and/or a lentivirus into the host cells. Accordingly, the present invention may further relate to a method of inhibiting the entry of an enterovirus and/or a lentivirus into host cells, comprising contacting the host cells with an effective amount of berbamine or its analogue as described above. The enterovirus may be EV-A71, and the lentivirus may encode histone B-RFP.

Still further, the present invention relates to use of berbamine or its analogue in prevention or treatment of a RNA virus infection as described above, and use in the preparation of a medicament for preventing or treating of a RNA virus infection as described above.

EXAMPLES

Assay for Detecting Viral Infection

Figure 1B:
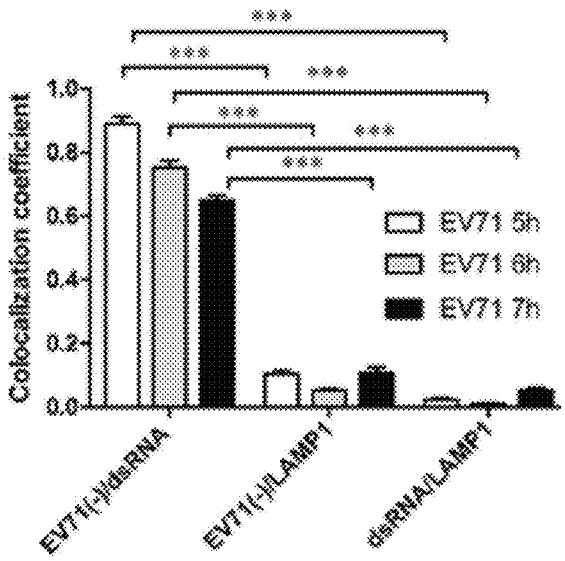
FIG. 1B is a plot prepared based on the results in FIG. 1A, demonstrating the colocalization coefficient of the EV-71 positive strand RNA and EV71 negative strand RNA in the infected cells.

The inventors established an assay for detecting viral infection. The inventors performed RNA in situ hybridization to detect both positive (+) and negative (−) strand virus RNA in the host cells after EV-A71 infection. As shown in FIG. 1A, both EV-A71 positive and negative RNA strands were detected after 7 h virus infection of HeLa cells. EV-A71 (−) RNA strand exhibited subtle co-localization with EV-A71 (+) RNA strand. On the other hand, double-stranded RNA, as shown by double-stranded RNA (DsRNA) immunostaining, exhibited strong co-localization with virus (−) RNA strand, not LAMP1, a lysosomal marker. Besides, DsRNA and (+) RNA were accumulated in time-dependent manner after virus infection (as shown in FIG. 1B). Thus, DsRNA immunostaining and viral specific (+) RNA hybridization can be applied to measure viral RNA replication.

Figure 1C:
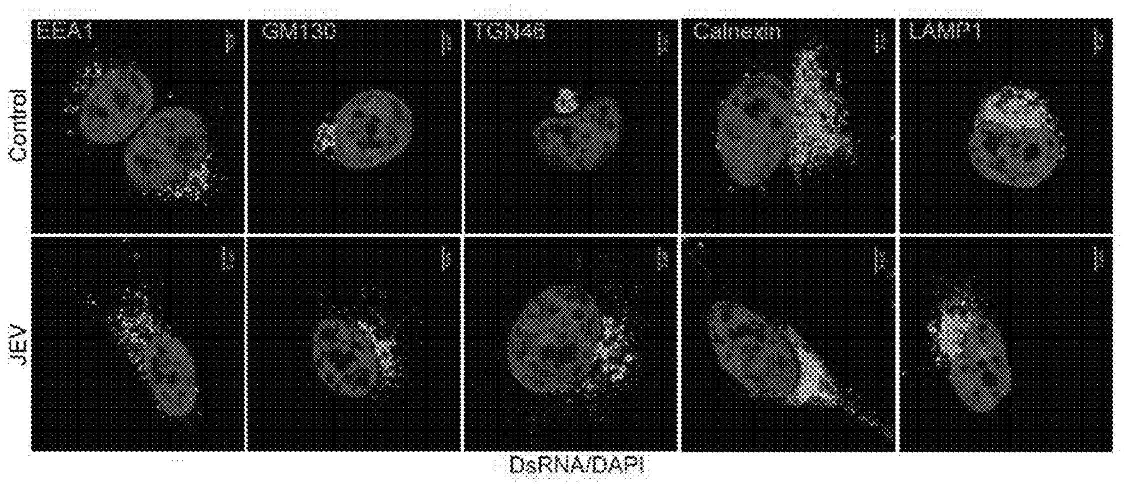
FIG. 1C shows the microscopic images of A549 cells, in which the A549 cells were infected with 10 MOI of JEV for 12 h, and stained with anti-double stranded RNA antibody and antibodies against different organelle markers, including early endosome marker EEA1, cis-golgi marker GM130, tran-golgi network marker TGN46, endoplasmic reticulum marker Calnexin, and lysosome marker LAMP1.

Besides EV-A71, the inventors also performed the aforementioned assays to measure ZIKV, JEV and DENV infection. The inventors particularly examined the localization of the virus replication in host cells by co-immunostaining the host cells after JEV infection with DsRNA antibody and antibodies against different organelle markers. As shown in FIG. 1C, DsRNA signal exhibited weak co-localization with early endosome (anti-EEIA staining), Golgi, endoplasmic reticulum (anti-Calnexin staining), or lysosome (anti-LAMP1 staining). These data suggested that JEV replication complex is located at a novel membrane structure in the host cell.

Accordingly, the inventors have established a valid immunostaining and a valid RNA hybridization assay to measure positive single strand RNA virus replication. This assay was applied to determine the antiviral effect of alkaloids against various viral infections, which is described in detail below.

Determination of the Role of $Ca^{2+}$ Signaling in Viral Infection

Figure 1D:
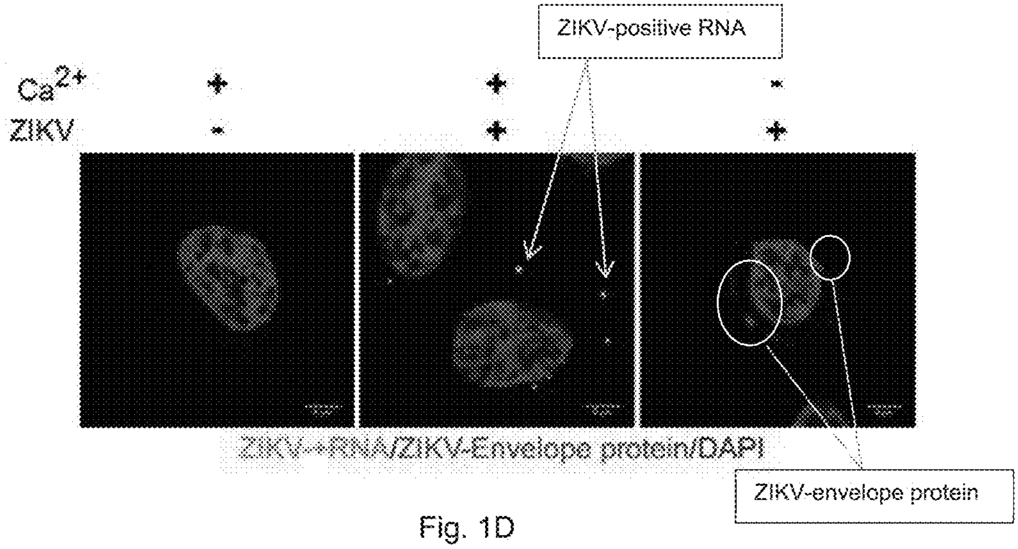
FIG. 1D shows the microscopic images of A549 cells infected with ZIKV in the presence or absence of extracellular calcium ions.

The inventors determined whether removal of extracellular $Ca^{2+}$ affects ZIKV infection of host cells by performing ZIKV H+RNA hybridization and anti-ZIKV envelope protein immunostaining. As shown in FIG. 1D, ZIKV+RNA was detectable inside host cells after 90 minutes of viral infection in the presence of extracellular $Ca^{2+}$, whereas no positive viral RNA was detected in host cells after 90 minutes of the viral infection in the absence of extracellular $Ca^{2+}$. Moreover, in the host cells in the absence of extracellular $Ca^{2+}$, intact virirons (staining with ZIKV envelope proteins) were detected in the plasma membrane of host cells as shown in the right panel of FIG. 1D. These results suggest that $Ca^{2+}$ influx is required for flavivirus entry of host cells.

Figure 1E:
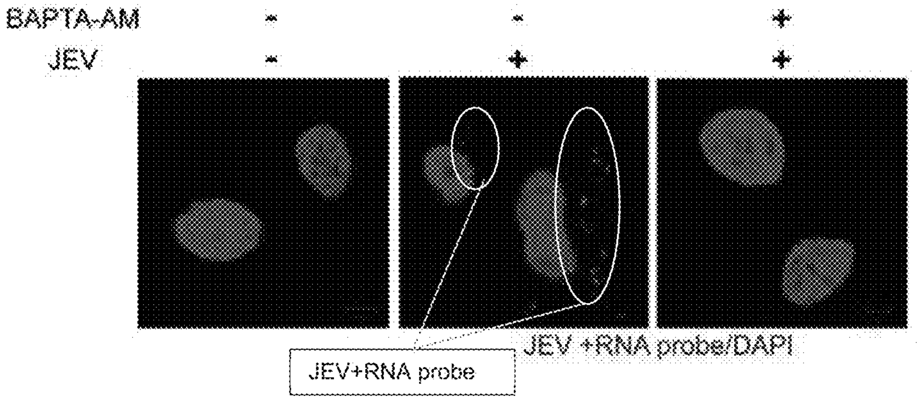
FIG. 1E shows the microscopic images of A549 cells infected with JEV after treatment with BAPTA-AM, a calcium chelator, in which the presence of absence of JEV positive RNA strand is detected.
Figure 1F:
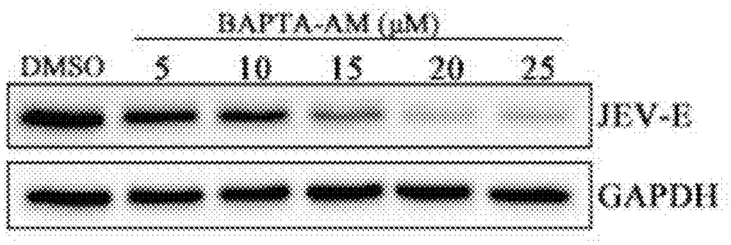
FIG. 1F is a Western blot pattern showing that BAPTA-AM treatment inhibited the JEV envelope protein synthesis in the A549 cells in a dose dependent manner.

With reference to FIG. 1E, in cells treated with BAPTA-AM, a calcium chelator, no ZIKV positive RNA strand was spotted inside the host cells. It was also found that BAPTA-AM treatment of host cells markedly inhibited the expression of JEV envelope protein in a dose dependent manner, as shown in FIG. 1F. Again, these date suggest that intracellular calcium signaling is involved in flavivirus infection of host cells. Similar data have also been observed for EV-A71 infection of host cells (data not shown). These data together support the role of $Ca^{2+}$ influx or intracellular $Ca^{2+}$ in flavivirus or enterovirus infections.

High-Content Image Based Assay for Measuring Viral Infection

Figure 2A:
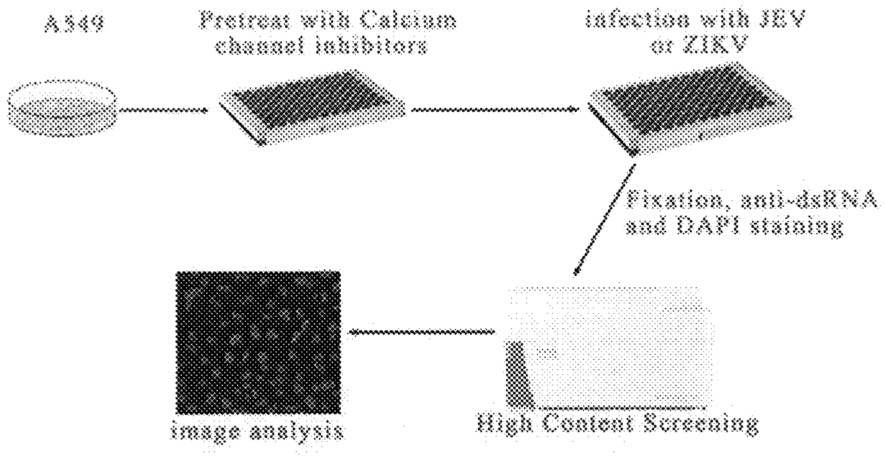
FIG. 2A illustrates the high-content image assay based on DsRNA immunostaining performed by the user for the purpose of measuring viral infection in host cells.

To measure flavivirus or enterovirus infection of host cells, the inventors developed a high-content image assay to measure DsRNA staining of virus infected cells by an automatic fluorescence microscopy, thereby quantifying flavivirus or enterovirus infection. The scheme of the measurement is illustrated in FIG. 2A. Particularly, the cells are pre-treated with a calcium channel inhibitor before being subject to viral infection. After viral infection, the cells are fixed. DsRNA immunostaining is then performed on the fixed cells, followed by high-content screening and image analysis.

This assay was then applied to screen compounds affecting viral infection, as follows. Host cells, e.g. A549, RD, PC3, or JEG-3 cells, were seeded in 96-well plates in triplicates, and cells were then pretreated with different compounds at different concentrations for 1 h before being infected with about 10 to about 100 MOI of JEV, ZIKV, or EV-A71 virus. After 8 to 24 h of infection, cells were fixed with 4% PFA and subject to DsRNA immunostaining and DAPI staining. The images were finally captured by CellInsight CX7 High-Content Screening platform with a 20× objective lens, and analyzed in HCS Studio™ 3.0 (Thermo Fisher, Waltham, MA, USA) to quantify the percentage of infected cells versus uninfected cells.

Figure 2B:
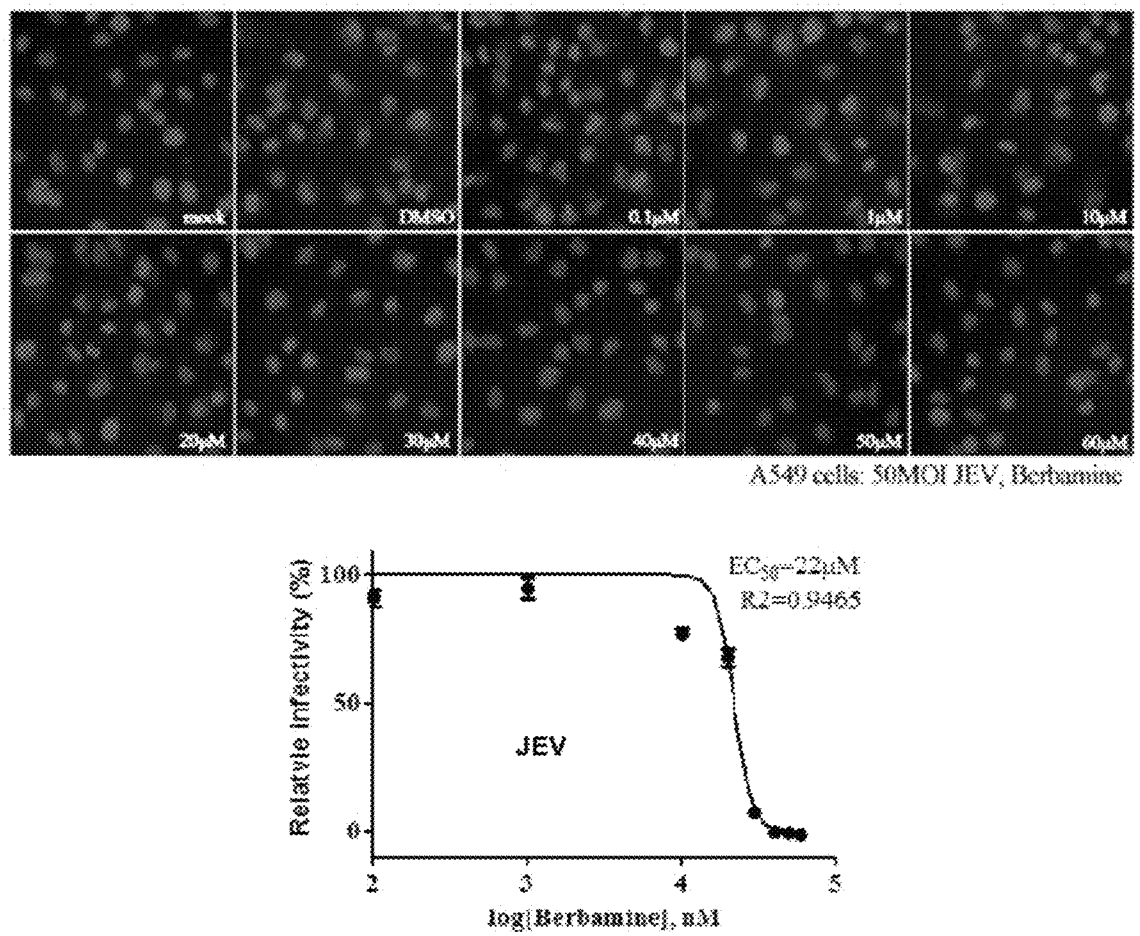
FIG. 2B shows the high-content images of A549 cells after pretreating A549 cells with indicated dose of berbamine for 1 h and infected with 50 MOI of JEV for 18 h, and a dose responsive curve of berbamine on JEV.

Inhibitory Effect of Berbamine and its Analogues Against ZIKV or JEV Infection The inventors determined the anti-infection activity of berbamine, a bis-benzylisoquinoline alkaloid isolated from the traditional Chinese medicine berberis, against ZIKV or JEV infection. As shown in FIG. 2B, berbamine, the alkaloid of Formula (I), significantly inhibited the infection of JEV in A549 cells, with $EC_{50}$ being 20 μM.

Formula (I)

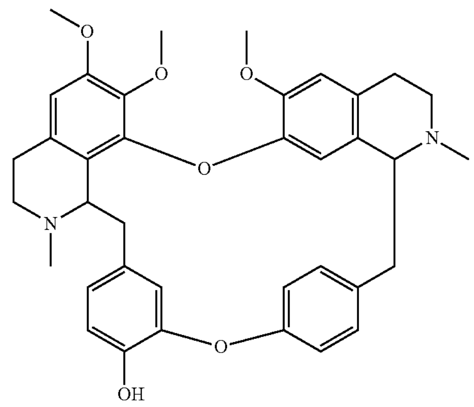

Figure 2C:
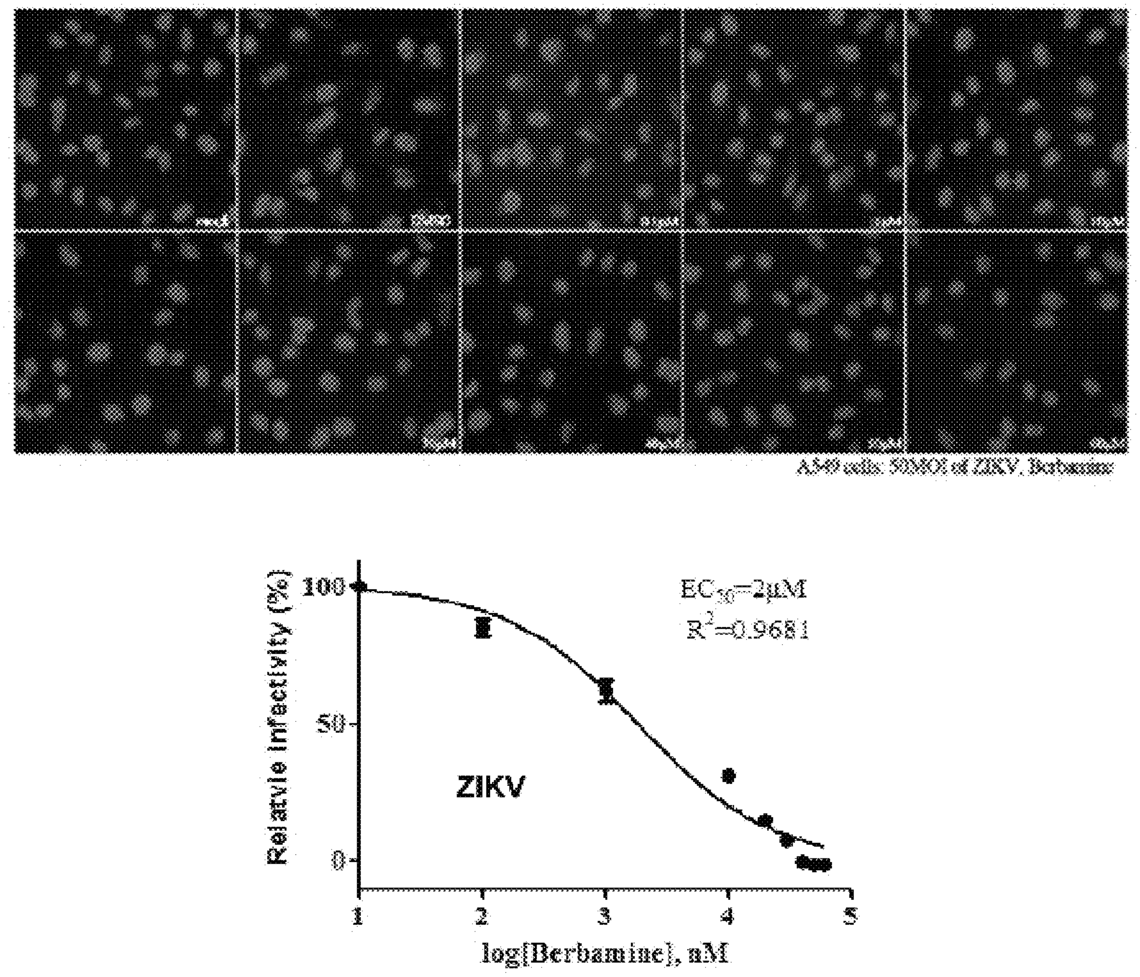
FIG. 2C shows the high-content images of A549 cells after pretreating A549 cells with indicated dose of berbamine for 1 h and infected with 50 MOI of ZIKV for 18 h, and a dose responsive curve of berbamine on ZIKV.
Figure 2D:
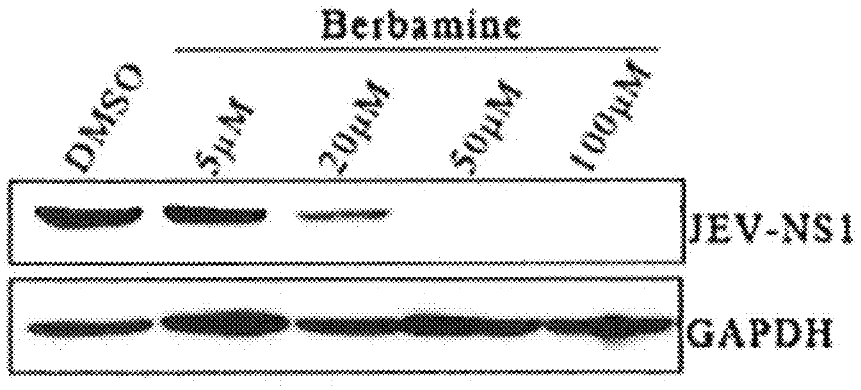
FIG. 2D is a Western blot pattern showing the expression of JEV-NS1 in A549 cells which were pretreated with berbamine at indicated dose for 1 h and infected with ~10 MOI JEV for 10 h, and the expression of JEV-NS1 in A549 cells which were pretreated with DMSO as control group.
Figure 2E:
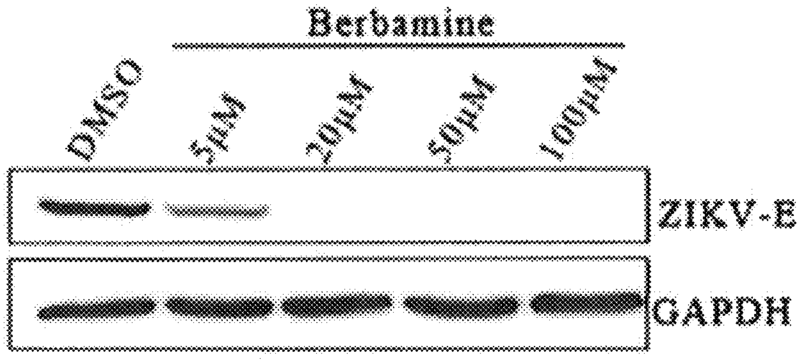
FIG. 2E is a Western blot pattern showing the expression of ZIKV-E in A549 cells which were pretreated with berbamine at indicated dose for 1 h and infected with ~10 MOI ZIKV for 10 h, and the expression of ZIKV-E in A549 cells which were pretreated with DMSO as control group.
Figure 2F:
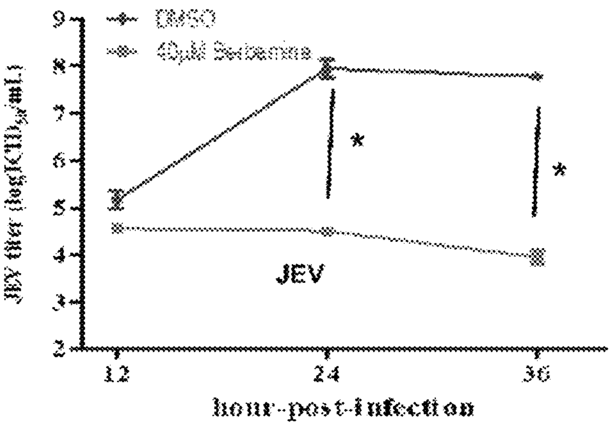
FIG. 2F is a plot of JEV titer against post-treatment time, after pretreating A549 cells with berbamine, in which berbamine markedly inhibited JEV virus production.
Figure 2G:
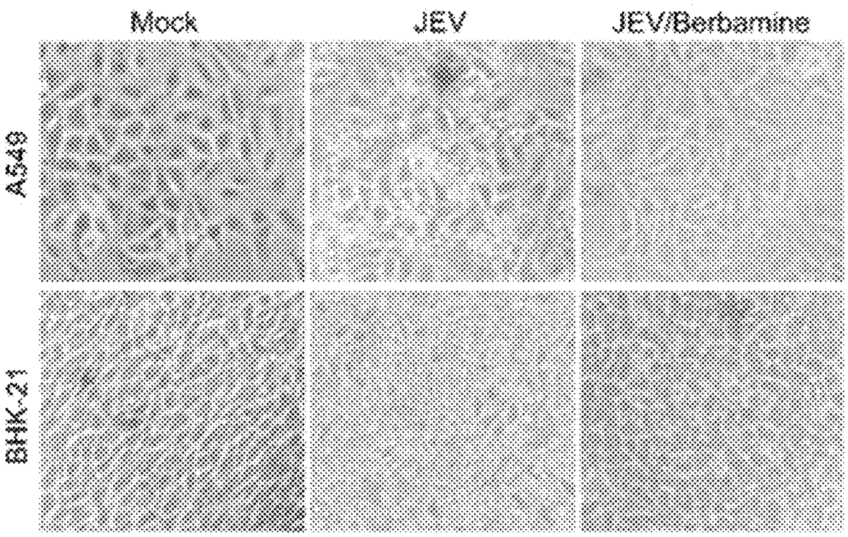
FIG. 2G includes microscopic images of A549 cells and BHK-21 cells after JEV infection with/without berbamine pretreatment.

FIG. 2C also demonstrates that berbamine inhibited the infection of ZIKV in A549 cells, with $EC_{50}$ being 2 μM. Moreover, as shown in FIGS. 2D and 2E, the pre-treatment of cells with berbamine markedly inhibited the protein expression of JEV-NSI and ZIKV-E in a dose dependent manner. The inventors further performed a virus titration assay and confirmed that pretreatment of cells with berbamine significantly inhibited the production of JEV according to the results in FIG. 2F. FIG. 2G also shows that the pretreatment of A549 cells or BHK-21 cells with berbamine markedly reduced JEV-induced cell death. These data indicated that berbamine has inhibitory effect against both JEV and ZIKV infection in host cells.

Figure 3A:
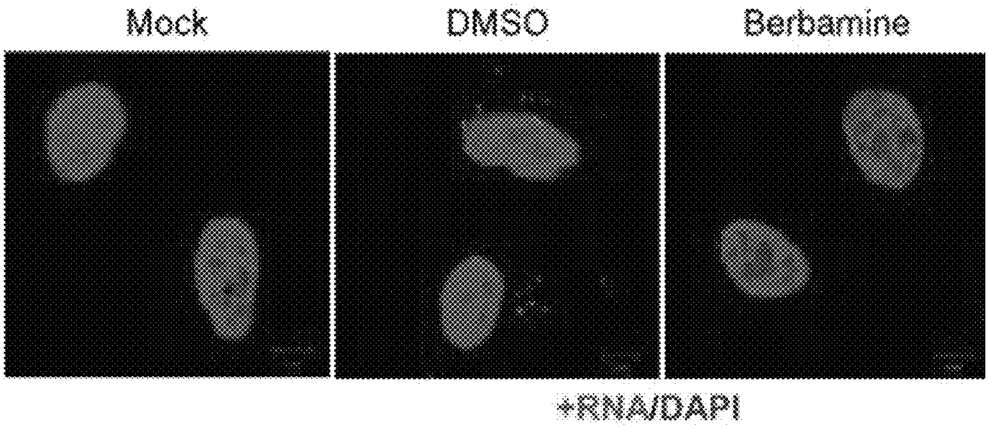
FIG. 3A shows the microscopic images of A549 cells after immunostaining, in which the cells were pretreated with berbamine for 1 h, then infected with 100 MOI of JEV for 80 min before fixation and staining. The encircled pattern refers to the presence of RNA genome of JEV.

Furthermore, as demonstrated in FIG. 1D, calcium influx is required for the entry of JEV or ZIKV. The inventors further determined whether treatment of host cells with berbamine can block the entry of these viruses. To evaluate this, A549 cells were pre-treated with berbamine for 1 h, and were then infected with JEV for 80 min before fixation. Viral positive strand RNA hybridization was subsequently performed to detect the RNA genome of JEV. The results in FIG. 3A show that the positive strand JEV RNA was only detected inside control cells, not in cells pretreated with berbamine.

Figure 3B:
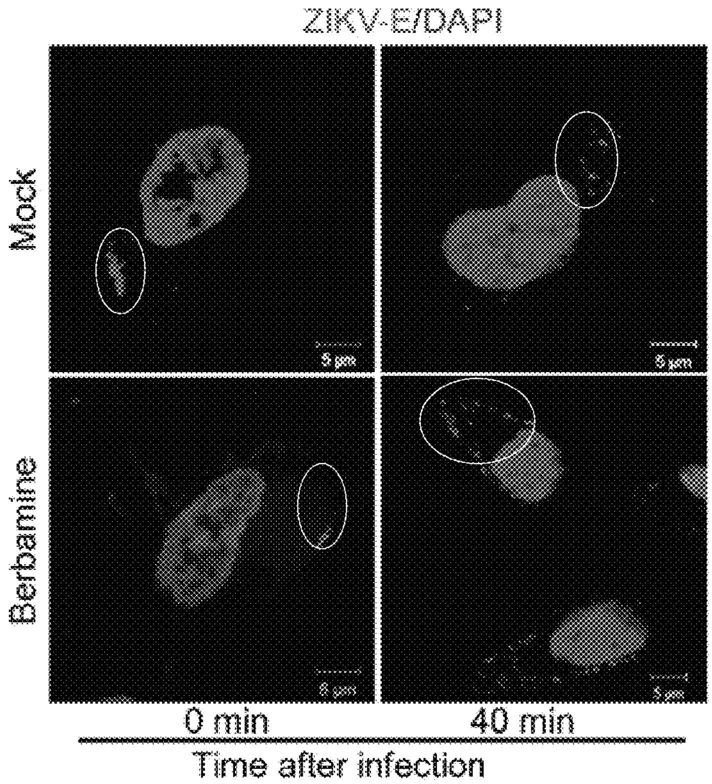
FIG. 3B shows the microscopic images of A549 cells after immunostaining, in which the cells were pretreated with berbamine, then infected with 100 MOI of ZIKV on ice for 1 h followed by incubation in warm medium for the indicated time course before fixation and staining. The arrows point to the presence of ZIKV.

Also, A549 cells pretreated with or without berbamine were incubated with ZIKV on ice for 1 h, and were then incubated with warm medium at 37° C. for another 40 min before fixation, followed by anti-ZIKV envelope protein immunostaining. The results in FIG. 3B show that the intact ZIKV virus (encircled in the figure) was detectable on the surface of virus infected cells pretreated with or without berbamine, whereas the intact ZIKV virus were highly concentrated at the surface of virus infected cells pretreated with berbamine, not the control cells, after cells were incubated at warm medium. Accordingly, these data demonstrate that berbamine have inhibitory effect against the entry of ZIKV or JEV into host cells.

The inventors further tested three analogues of berbamine including isotetrandrine, fangchinoline, and E6 berbamine to see if they have anti-infection effect against the flavivirus particularly JEV and ZIKV.

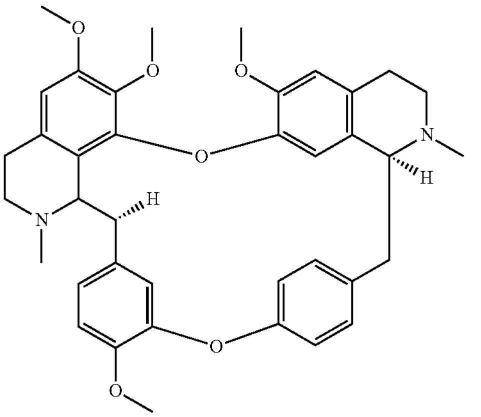

Isotetrandrine

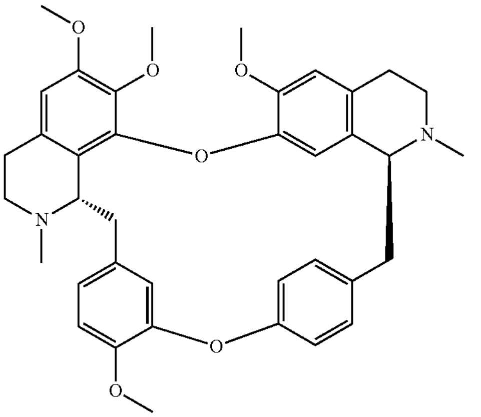

Fangchinoline

-continued

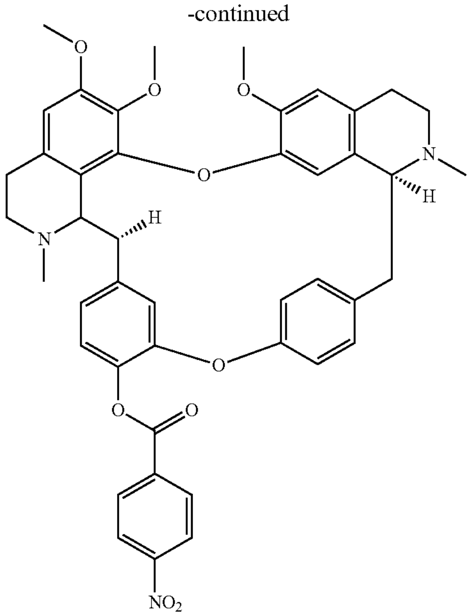

E6 berbamine

Figure 4A:
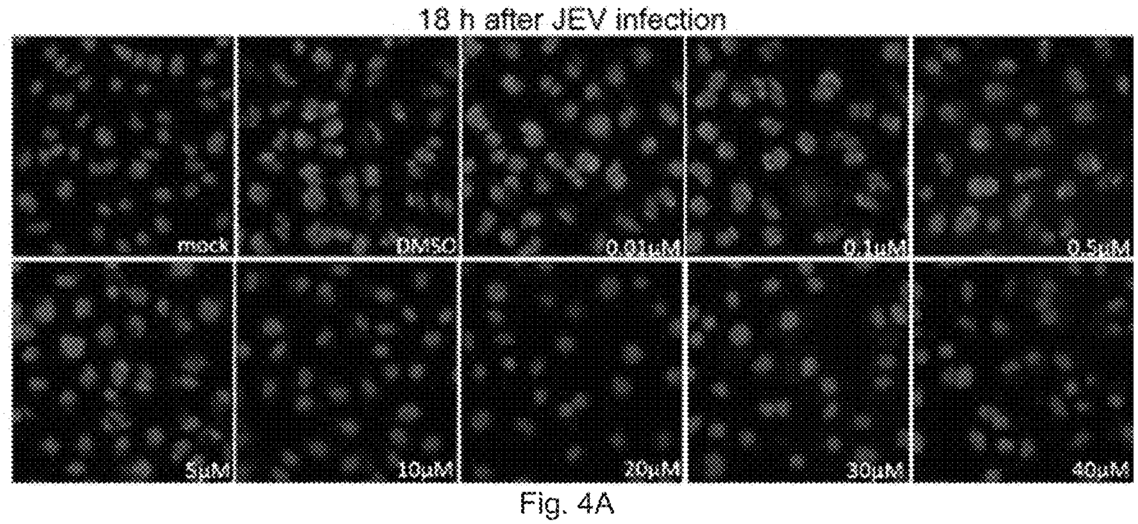
FIG. 4A shows the high-content images of A549 cells after immunostaining, in which the cells were pretreated with indicated doses of isotetrandrine for 1 h, then infected with about 50 MOI of JEV.
Figure 4B:
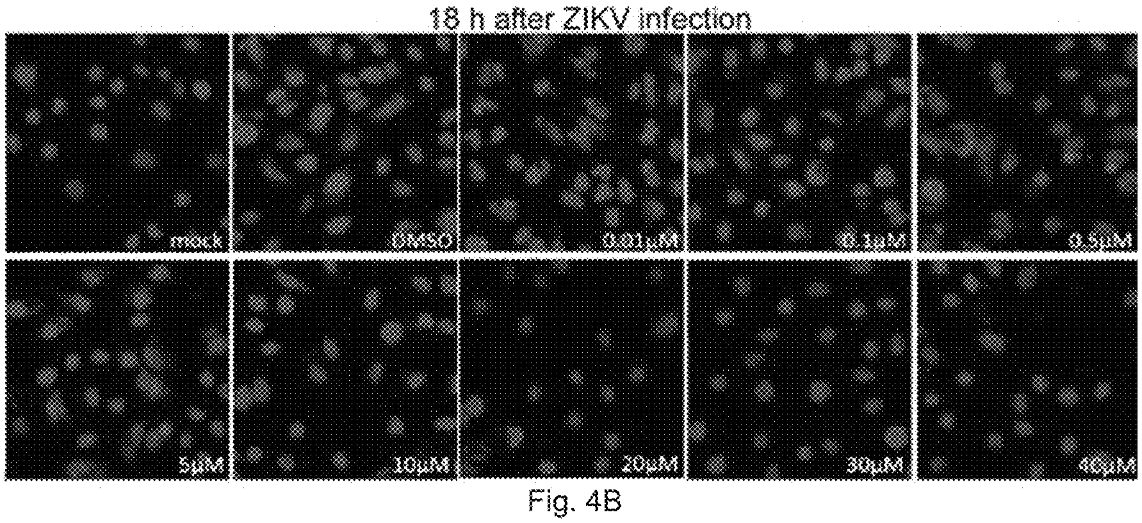
FIG. 4B shows the high-content images of A549 cells after immunostaining, in which the cells were pretreated with indicated doses of isotetrandrine for 1 h, then infected with about 50 MOI of ZIKV.
Figure 4C:
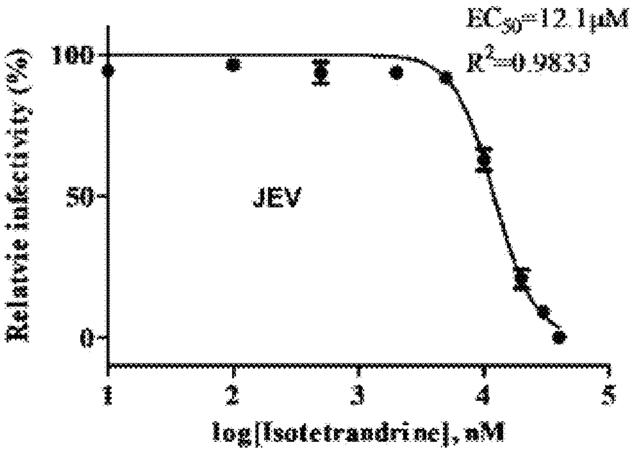
FIG. 4C is plot showing the relative infectivity of JEV in 549 cells in the treatment of isotetrandrine at different doses, wherein the $EC_{50}$ of isotetrandrine against JEV in A549 cells is around 12 μM.

As shown in FIGS. 4A to 4C, it was found that isotetrandrine significantly inhibited both JEV and ZIKV infections of host cells. Referring to FIG. 7C, the EC50 of isotetrandrine against JEV in A549 cells is around 12 μM.

Figure 5A:
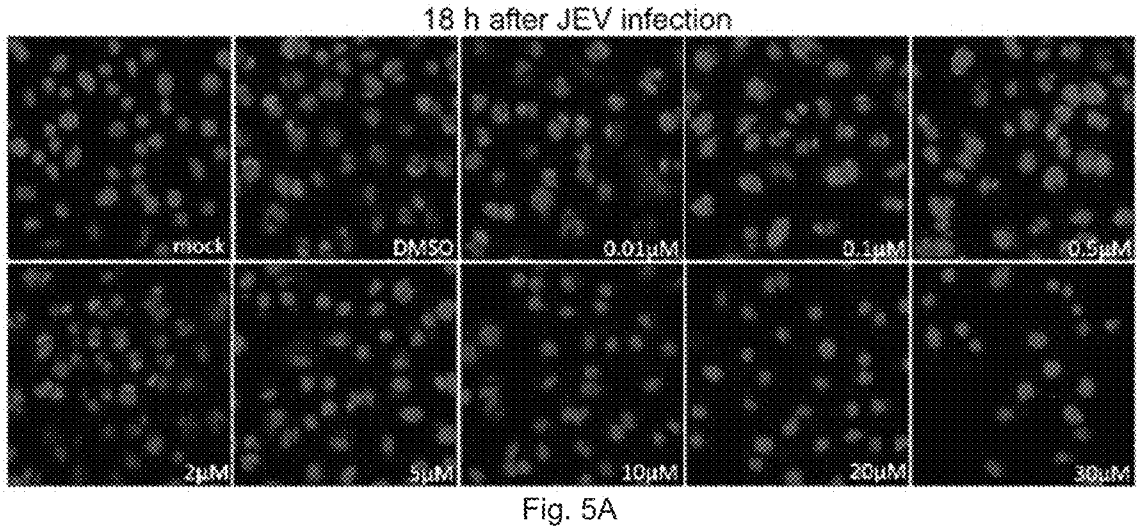
FIG. 5A shows the high-content images of A549 cells after immunostaining, in which the cells were pretreated with indicated doses of fangchinoline for 1 h, then infected with about 50 MOI of JEV.
Figure 5B:
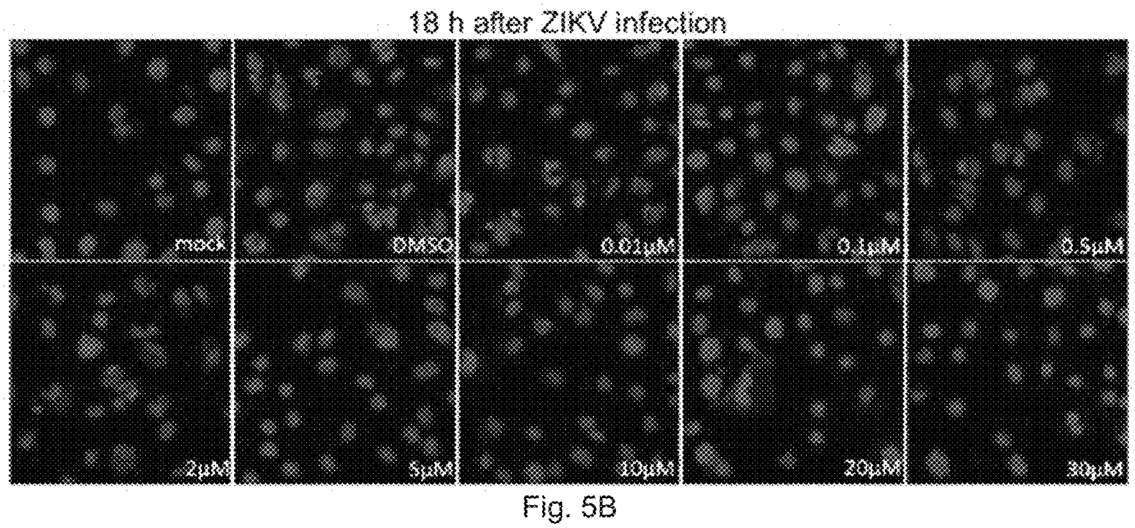
FIG. 5B shows the high-content images of A549 cells after immunostaining, in which the cells were pretreated with indicated doses of fangchinoline for 1 h, then infected with about 50 MOI of ZIKV.
Figure 5C:
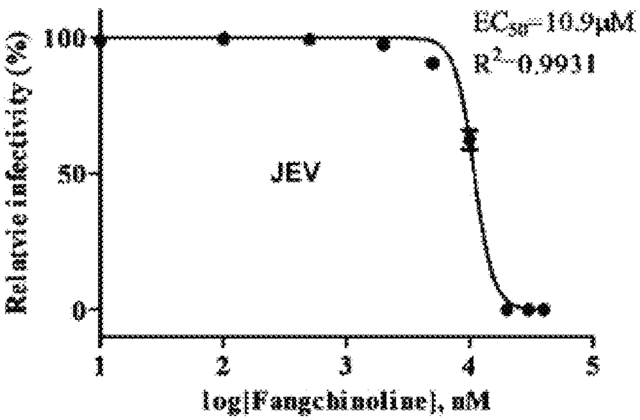
FIG. 5C is plot showing the relative infectivity of JEV in 549 cells in the treatment of fangchinoline at different doses, wherein the $EC_{50}$ of fangchinoline against JEV in A549 cells is around 11 μM.

As shown in FIGS. 5A to 5C, it was found that fangchinoline significantly inhibited both JEV and ZIKV infections of host cells. Referring to FIG. 8C, the EC50 of fangchinoline against JEV in A549 cells is around 11 μM.

Figure 6A:
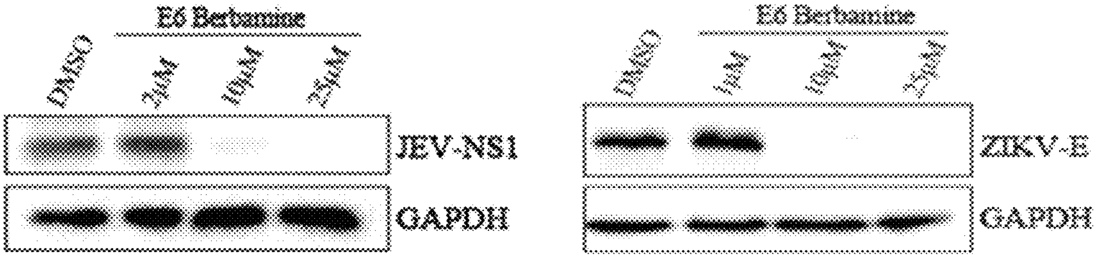
FIG. 6A is a Western blot pattern showing the expression of JEV-NS1 and ZIKV-E in A549 cells, in which the cells were pretreated with indicated doses of E6 berbamine for 1 h, then infected with about 50 MOI of JEV or ZIKV.

As shown in FIG. 6A, it was found that E6-berbamme markedly inhibited the infection of JEV or ZIKV, as manifested by strong inhibition of JEV-NSI and ZIKV-Envelope protein expression in host cells treated with E6-berbamine.

Figure 6B:
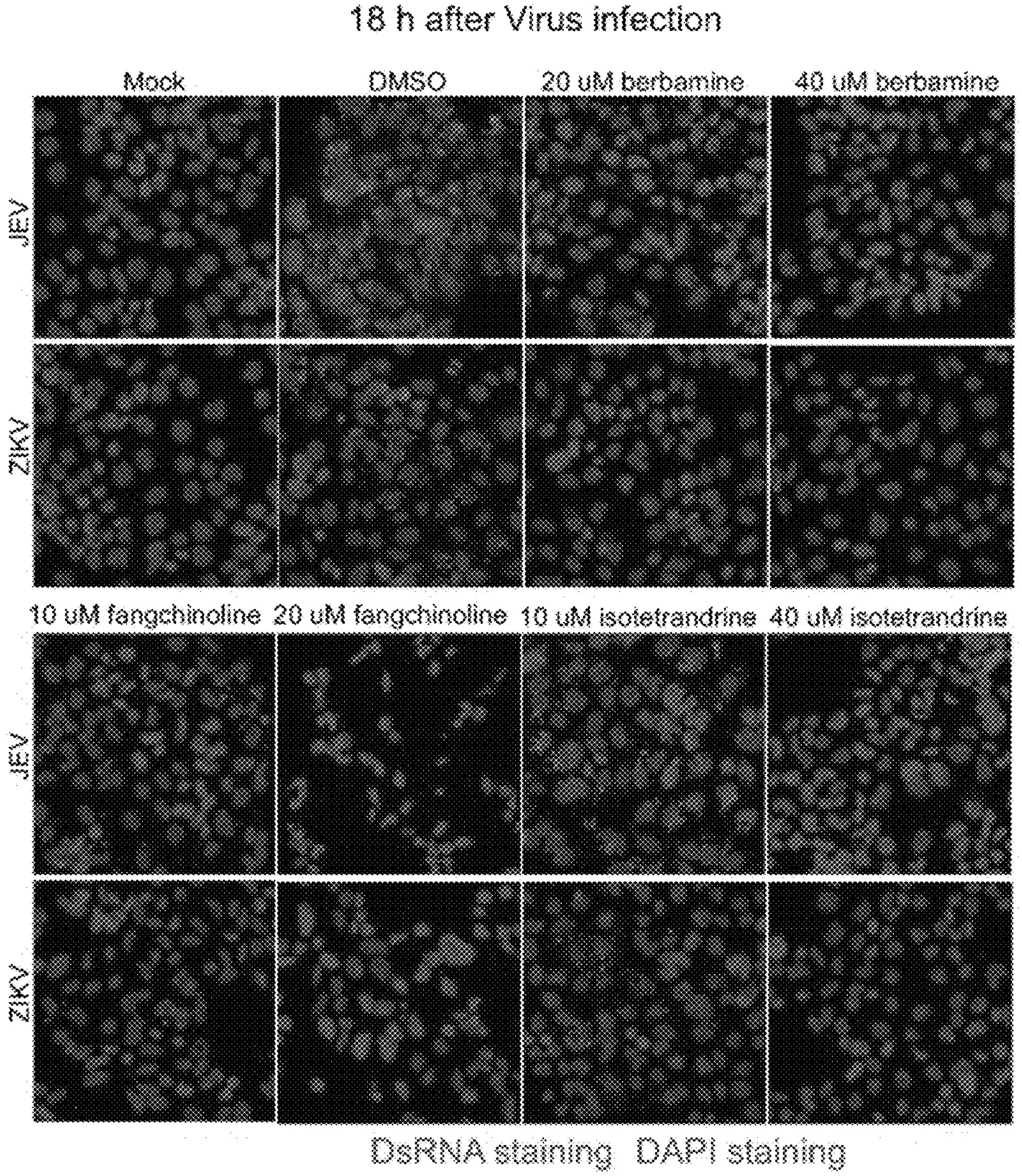
FIG. 6B shows the high-content images of JEG-3 cells after immunostaining, in which the cells were pretreated with 20 μM of berbamine, 40 μM of berbamine, 10 μM of fangchinoline, 20 μM of fangchinoline, 10 μM of isotetrandrine or 40 μM of isotetrandrine for 1 h, then infected with about 50 MOI of JEV or ZIKV for 18 h.

Moreover, the inventors determined their effect against JEV or ZIKV infection in another host cell line to ensure their anti-viral effects are not cell type specific. Referring to FIG. 6B, treatment of JEG-3 cells with berbamine, isotetrandrine, fangchinoline, and E6 berbamine all significantly inhibited JEV or ZIKV infection as shown by DsRNA immunostaining followed by high-content image analysis. Taken together, these data demonstrate that bis-benzylisoquinoline alkaloids are potent anti-JEV or anti-ZIKV agent in vitro.

Inhibitory Effect of Berbamine and its Analogues Against DENV Infection

The inventors also studied whether berbamine and its analogues have any effects on DENV infection. Briefly, A549 cells plated in triplicates in 96-well plates were pretreated with different doses of berbamine (5 μM, 15 μM or 30 μM), fangchinoline (10 μM, 20 μM or 30 μM) or isotetrandrine (10 μM, 20 μM or 40 μM) for 1 h before infected with about 10 MOI of Dengue virus type 2 (DENV-2). Cells were then fixed at 24 h.p.i. and subjected to DsRNA immunostaining to detect DENV-2 replication.

Figure 7A:
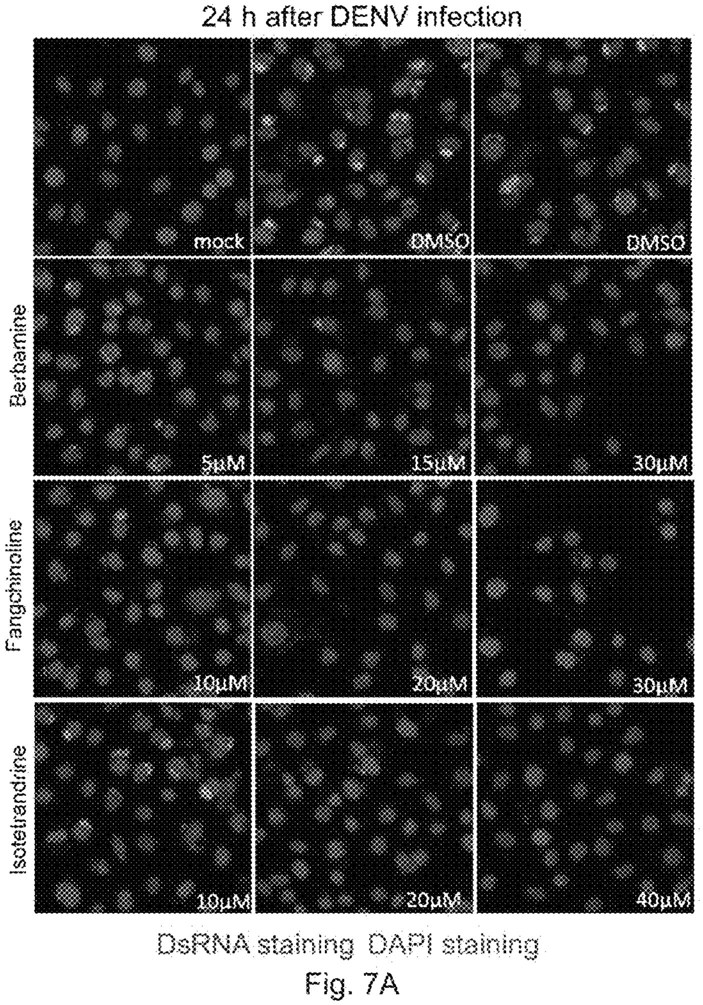
FIG. 7A shows the high-content images of A549 cells after immunostaining, in which the cells were pretreated with 5 μM of berbamine, 15 μM of berbamine, 30 μM of berbamine, 10 μM of fangchinoline, 20 μM of fangchinoline, 30 μM of fangchinoline, 10 μM of isotetrandrine, 20 μM of isotetrandrine or 40 μM of isotetrandrine for 1 h, then infected with about 10 MOI of DENV-2 for 18 h. High-content images of A549 cells of a control group pretreated with DMSO are also illustrated.
Figure 7B:
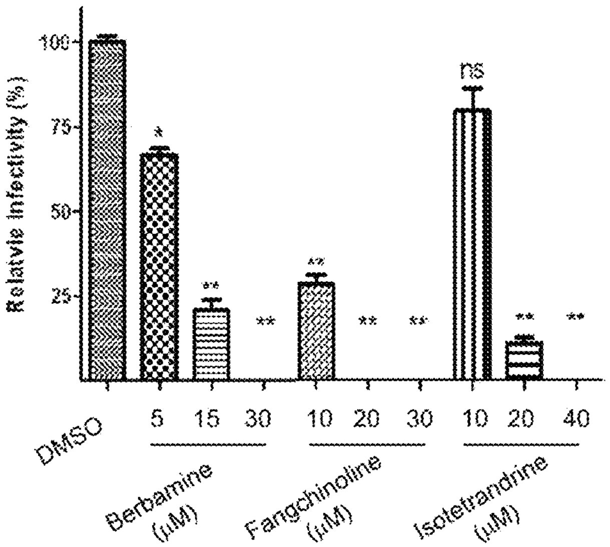
FIG. 7B is a plot showing the relative infectivity of DENV-2 in A549 cells, in which the cells were pretreated with indicated doses of berbamine, fangchinoline, or isotetrandrine for 1 h, then infected with about 10 MOI of DENV-2.

As shown in FIGS. 7A and 7B, all berbamine, isotetrandrine, and fangchinoline can significantly inhibit DENV-2 infection in A549 cells in a dose dependent manner. Taken together, these data demonstrate that berbamine and its analogues are potent anti-DENV agents and may be used as pan-anti-flavivirus agents.

Identification of Compounds with a Similar Structure by Virtual Screening
The inventors identified further 13 compounds via ligand-based virtual drug screening by using berbamine as reference. The identified 13 compounds are listed below.
TABLE 1
| Identified additional compounds | |
|---|---|
| 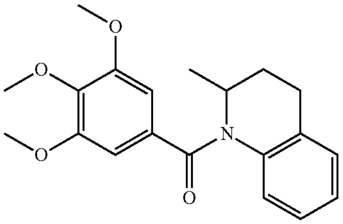 | #1 |
| 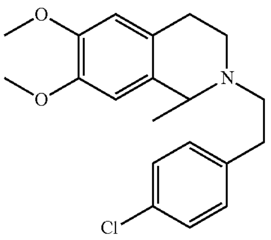 | #2 |
| 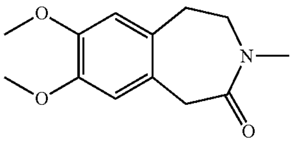 | #3 |
| 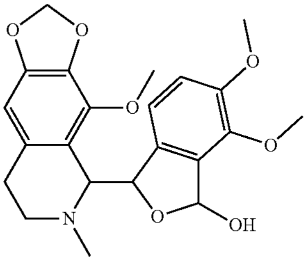 [SMILES: COc1ccc2c(c1OC)C(O)OC2C1c2c(cc3c(c2OC)OCO3)CCN1C] | #4 |
| 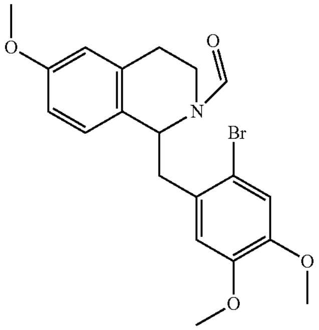 [SMILES: COc1ccc2c(c1)CCN(C=O)C2Cc1cc(OC)c(OC)cc1Br] | #5 |
TABLE 1-continued
| Identified additional compounds | |
|---|---|
| 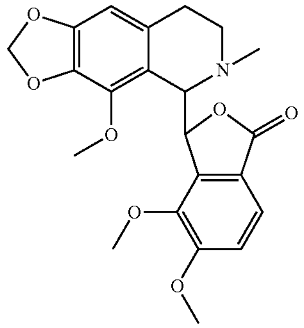 [SMILES: COc1ccc2c(c1OC)C(C1c3c(cc4c(c3OC)OCO4)CCN1C)OC2=O] | #6 |
| 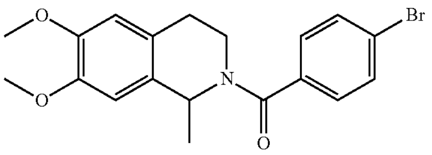 [SMILES: COc1cc2c(cc1OC)C(C)N(C(=O)c1ccc(Br)cc1)CC2] | #7 |
| 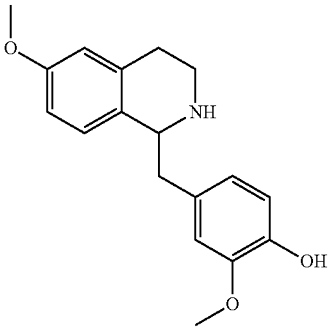 [SMILES: COc1ccc2c(c1)CCNC2Cc1ccc(O)c(OC)c1] | #8 |
| 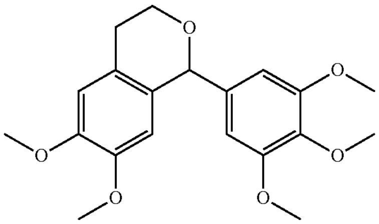 | #9 |
| 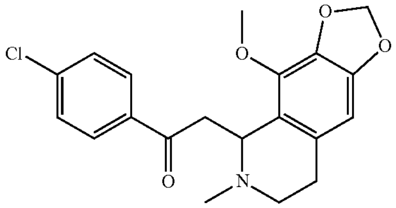 [SMILES: COc1c2c(cc3c1C(CC(=O)c1ccc(Cl)cc1)N(C)CC3)OCO2] | #10 |
| 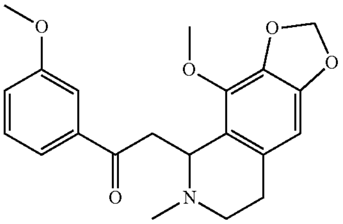 [SMILES: COc1cccc(C(=O)CC2c3c(cc4c(c3OC)OCO4)CCN2C)c1] | #11 |

TABLE 1-continued

Identified additional compounds

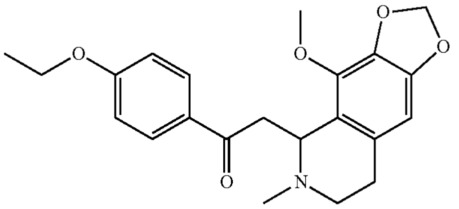 [SMILES: CCOc1ccc(C(=O)CC2c3c(cc4c(c3OC)OCO4)CCN2C)cc1]

#12

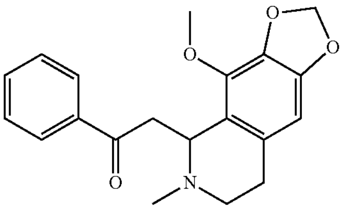 [SMILES: COc1c2c(cc3c1C(CC(=O)c1ccccc1)N(C)CC3)OCO2]

#13

Figure 8A:
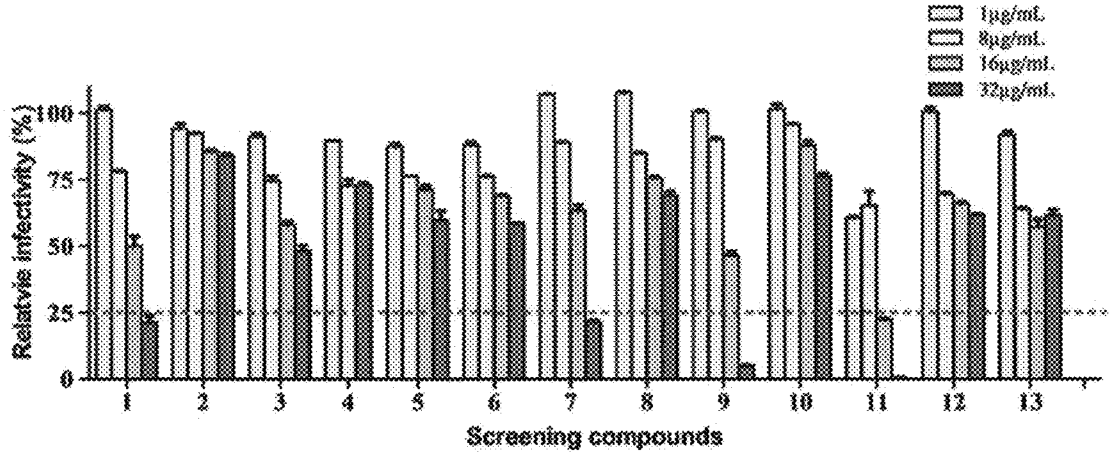
FIG. 8A is a plot showing the relative infectivity of JEV in A549 cells pretreated with 13 additionally identified compounds.
Figure 8B:
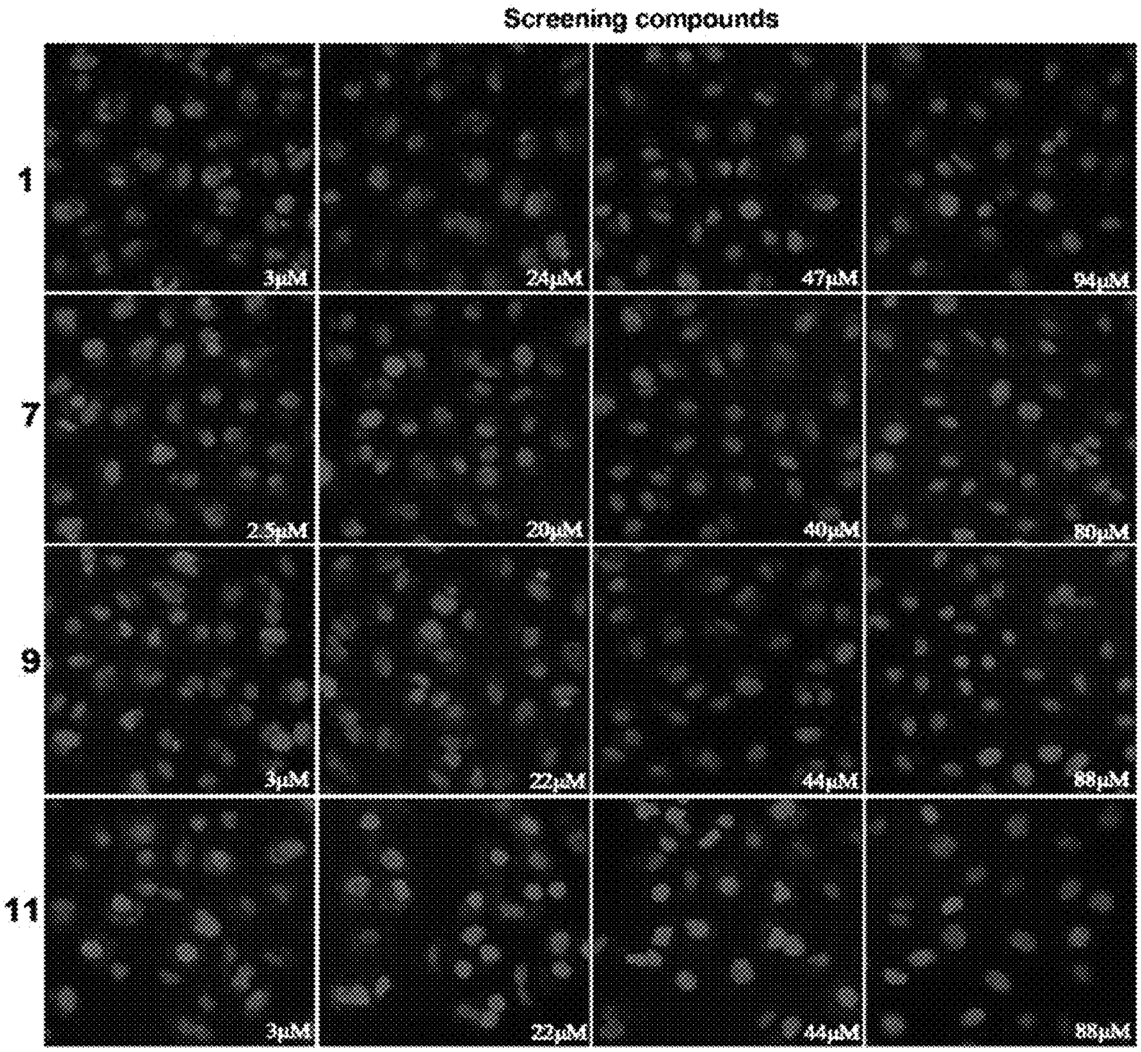
FIG. 8B shows the high-content images of A549 cells after immunostaining, in which the cells were pretreated with Compound #1, Compound #7, Compound #9 or Compound #11 respectively, then infected with about 50 MOI of JEV.

As shown in FIG. 8A, all these compounds have demonstrated an inhibitory effect against JEV infection in A549 host cells. Among them, 4 compounds including Compound #1, #7, #9 and #11 exhibited highest potency. As shown in FIG. 8B, these 4 compounds can effectively block the entry of JEV into the host cells.

Antiviral Effect Against JEV in Mice

Figure 9A:
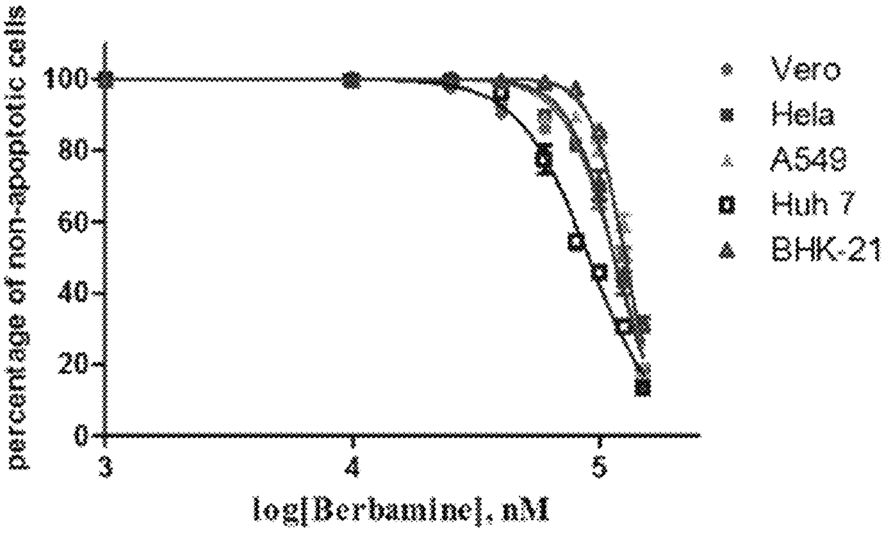
FIG. 9A shows the cytotoxicity of berbamine in A549 cells, BHK-21 cells, Vero cells, Hela cells, and Huh 7 cells.

The inventors determined the cytotoxicity of berbamine in different cell lines including A549 cells, BHK-21 cells, and RD cells. As shown in FIG. 9A and Table 2, it was found that berbamine has lowest cytotoxicity but highest therapeutic index as compared to other alkaloids (Table 3). The inventors therefore assessed the anti-JEV effects of berbamine in a mouse model.

TABLE 2

Cytotoxicity of berbamine in various cell lines.

| Cell Type | $CC_{50}$ (μM) |
|---|---|
| Vero | 114.936 ± 5.297 |
| Hela | 114.762 ± 3.596 |
| A549 | 126.629 ± 3.896 |
| Huh7 | 90.436 ± 2.977 |
| BHK-21 | 126.841 ± 2.426 |

TABLE 3

Selectivity index

| Virus | Selective Index ($CC_{50}/EC_{50}$) |
|---|---|
| ZIKV | 63.3 |
| JEV | 5.7 |
| EV71 | 7.3 |

Figure 9B:
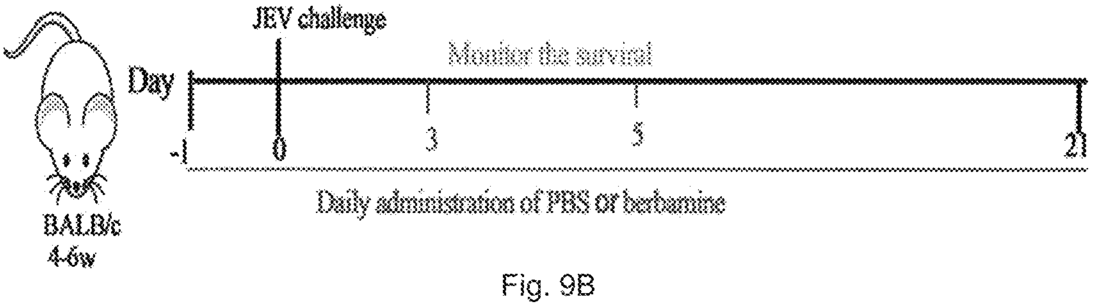
FIG. 9B illustrates the animal experiment, in which mice were injected with JEV, and then administered with PBS as the control group or berbamine as the treatment group.

As illustrated in FIG. 9B, adult female BALB/c mice (age, 4 to 6-week) mice were randomly divided into two groups (7 mice per group): a JEV-infected with vehicle-treated group and a JEV-infected with berbamine-treated group. For infection, mice were injected intraperitoneally with approximately $10^{6.5}$ $TCID_{50}$ of JEV. For the berbamine treatment group, mice were injected intraperitoneally with a dose of 50 mg/kg berbamine or PBS daily. For the control-vehicle group, mice were injected intraperitoneally with a dose of 50 mg/kg PBS daily. Survival rate and change of body weight if the mice in each group were monitored for 15 days after JEV injection.

Figure 9C:
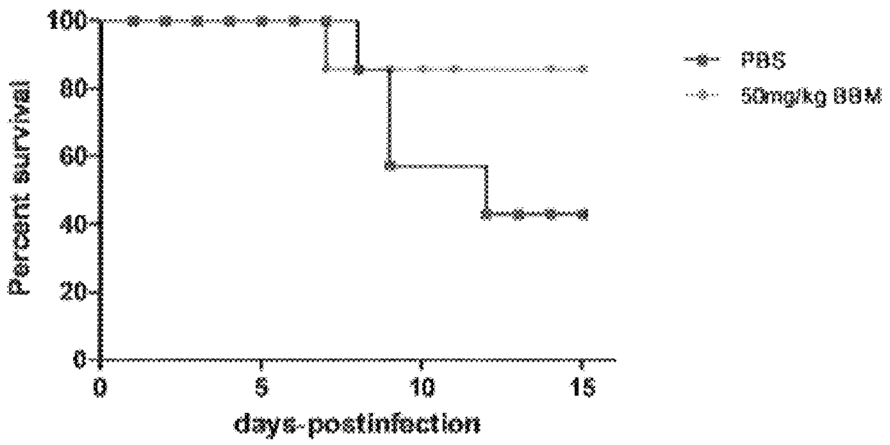
FIG. 9C shows the survival rate of mice after JEV challenge followed by treatment of berbamine for 15 days.
Figure 9D:
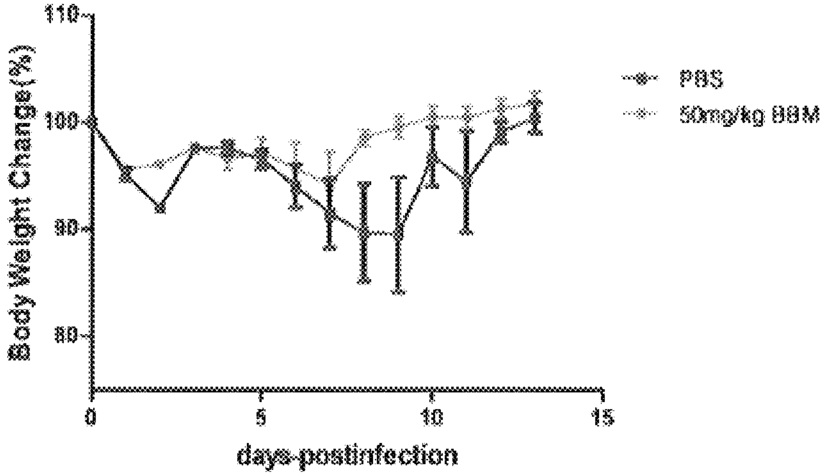
FIG. 9D shows the body weight change of mice after JEV challenge followed by treatment of berbamine for 15 days.

As shown in FIGS. 9C and 9D, berbamine treatment increases the survival rate of the mice, i.e. protect the mice from the lethal challenge of JEV. The higher survival rate and less weight changes in berbamine treatment group, as compared to the control group, further suggest that berbamine is a potential anti-flavivirus drug against JEV.

Inhibitory Effect of Berbamine and its Analogues Against Other RNA Virus Infection In addition, other than flavivirus infection, the inventors determined whether berbamine has any antiviral effect against enterovirus and lentivirus infection, by applying the same high-content image based assay as discussed above.

Figure 10:
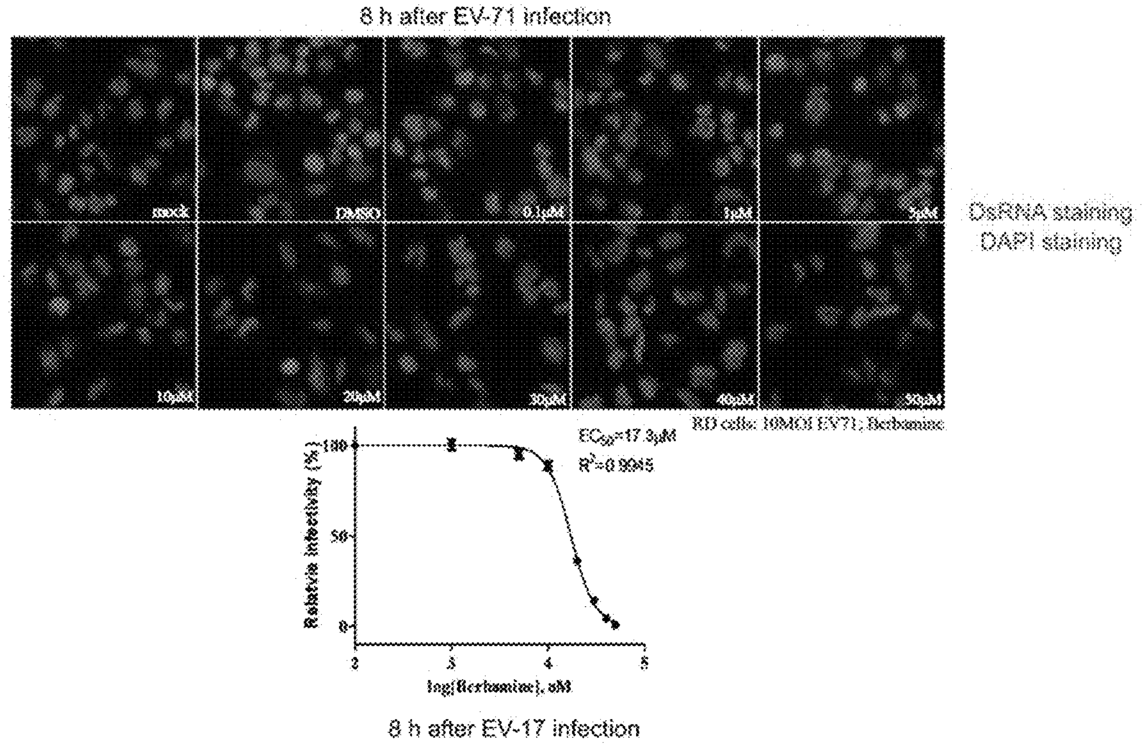
FIG. 10 shows the high-content images of RD cells after immunostaining, in which the cells were pretreated with berbamine with the indicated doses, and then infected with 10 MOI of EV-71, as well as a plot of relative infectivity of EV-71 in the pretreated cells with $EC_{50}$ being about 17.3 μM.

As shown in FIG. 10, berbamine treatment of RD cells significantly inhibited EV-A71 infection, with $EC_{50}$ being around 17 μM.

Figure 11:
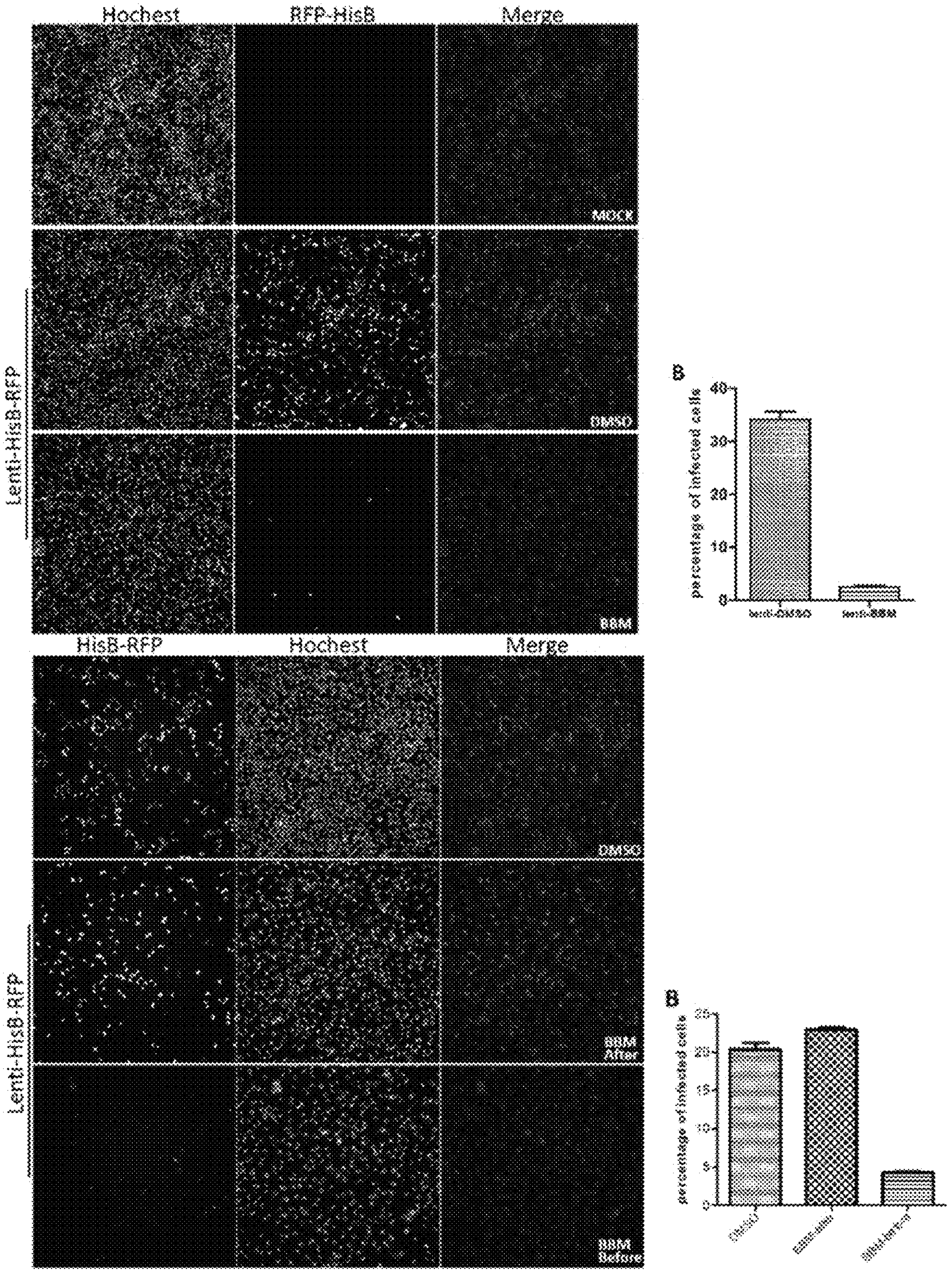
FIG. 11 shows the high-content images of A549 cells after immunostaining, in which the cells were pretreated with berbamine, and then infected with lentivirus encoding histone B-RFP; and the corresponding quantitative plot.

Further, pretreatment of A549 cells with berbamine also abolished lentivirus infection, as shown in FIG. 11.

Based on the above experimental results, it has been demonstrated that berbamine and its analogues particularly berbamine are potential anti-RNA virus agents.

The invention claimed is:

1. A method of preventing or treating a subject suffering from an enterovirus or a lentivirus infection by administering an effective amount of berbamine or its analogue to the subject, wherein berbamine has a structure of Formula (I):

Formula (I)

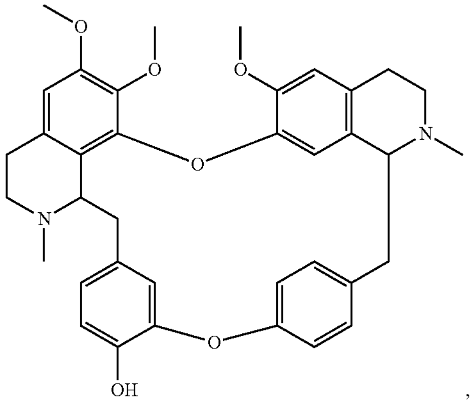

, and wherein said berbamine or its analogue inhibits the entry of an enterovirus and/or a lentivirus in host cells of the subject.

2. The method of claim 1, wherein the analogue of berbamine has a structure of Formula (II), (III), or (IV):

Formula (II)

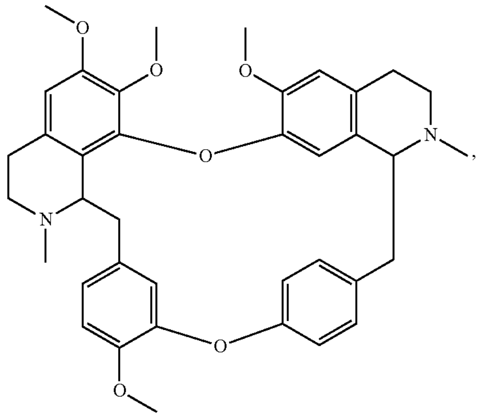

,

Formula (III)

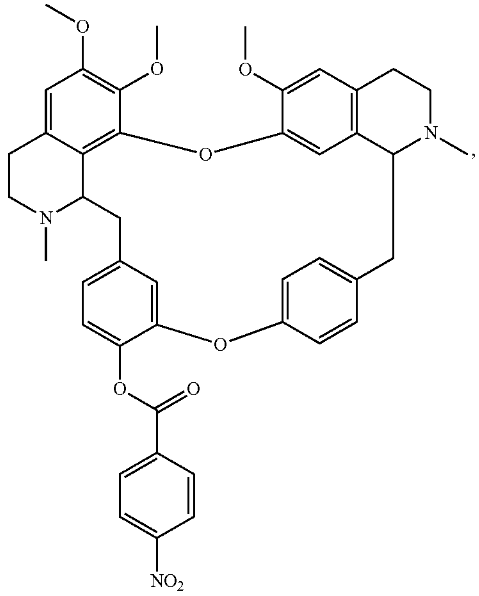

, or

Formula (IV)

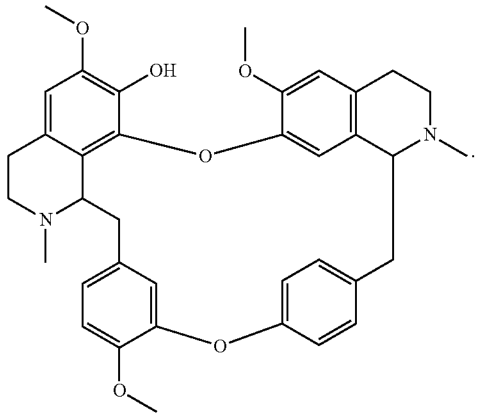

.

3. The method of claim 2, wherein the analogue of berbamine has a structure of Formula (IIb), (IIIb) or (IVb):

Formula (IIb)

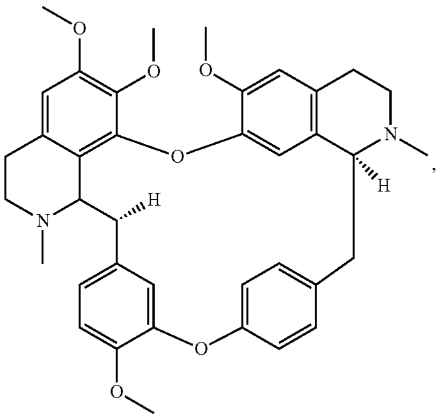

,

Formula (IIIb)

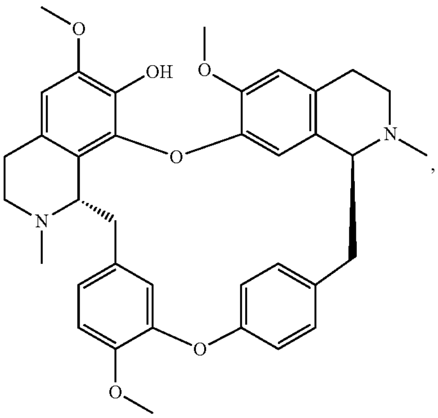

, or

Formula (IVb)

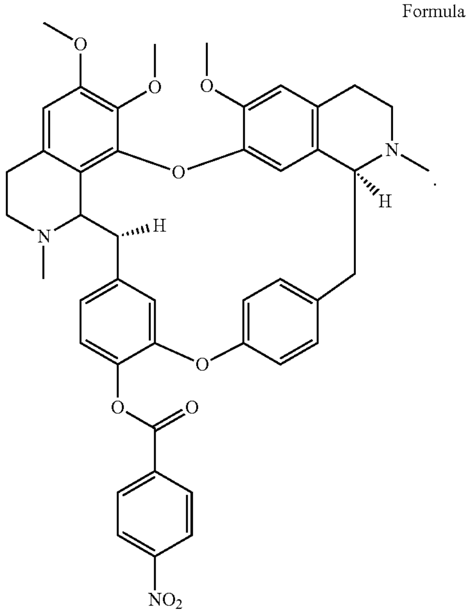

.

4. The method of claim 1, wherein berbamine or its analogue is administered to the subject by a route selected from a group consisting of oral delivery, intravenous delivery, intradermal delivery, intraperitoneal delivery and intramuscular delivery.

5. The method of claim 1, wherein the subject is a mammal and the berbamine or its analogue is administered to the subject at a dose of about 20 mg/kg to about 50 mg/kg.

6. The method of claim 1, wherein the subject is human and berbamine or its analogue is administered to the subject at a dose of about 20 mg/kg to about 50 mg/kg.

7. The method of claim 1, wherein the enterovirus is EV-A71.

8. The method of claim 1, wherein the lentivirus encodes histone B-RFP.

* * * * *

UNITED STATES PATENT AND TRADEMARK OFFICE

CERTIFICATE OF CORRECTION

PATENT NO. : 11,931,353 B2
APPLICATION NO. : 17/738291
DATED : March 19, 2024
INVENTOR(S) : Jianbo Yue and Lihong Huang It is certified that error appears in the above-identified patent and that said Letters Patent is hereby corrected as shown below:

On the Title Page

Item (54) The title and in the Specification Column 1, Lines 1-6 should read:
METHODS OF PREVENTING OR TREATING FLAVIVIRUS VIRUS INFECTIONS AND METHODS OF INHIBITING THE ENTRY OF FLAVIVIRUS, ENTEROVIRUS OR LENTIVIRUS INTO HOST CELLS Signed and Sealed this
Seventh Day of May, 2024

Katherine Kelly Vidal

Katherine Kelly Vidal
*Director of the United States Patent and Trademark Office*